US008084464B2

(12) United States Patent
Liu

(10) Patent No.: US 8,084,464 B2
(45) Date of Patent: Dec. 27, 2011

(54) TETRAHYDROISOQUINOLINE DERIVATIVES

(75) Inventor: Julie Liu, Lexington, MA (US)

(73) Assignee: CoNCERT Pharmaceuticals, Inc., Lexington, MA (US)

( * ) Notice: Subject to any disclaimer, the term of this patent is extended or adjusted under 35 U.S.C. 154(b) by 368 days.

(21) Appl. No.: 12/338,754

(22) Filed: Dec. 18, 2008

(65) Prior Publication Data

US 2009/0192188 A1 Jul. 30, 2009

Related U.S. Application Data

(60) Provisional application No. 61/014,635, filed on Dec. 18, 2007.

(51) Int. Cl.
*C07D 217/12* (2006.01)
*A61K 31/472* (2006.01)
(52) U.S. Cl. ........................................ 514/307; 546/146
(58) Field of Classification Search ........................ None
See application file for complete search history.

(56) References Cited

U.S. PATENT DOCUMENTS

| | | | |
|---|---|---|---|
| 6,221,335 B1 | 4/2001 | Foster | |
| 6,440,710 B1 | 8/2002 | Keinan et al. | |
| 6,603,008 B1 | 8/2003 | Ando et al. | |
| 6,916,830 B2 * | 7/2005 | Lee et al. | 514/317 |
| 7,517,990 B2 | 4/2009 | Ito et al. | |
| 2007/0082929 A1 | 4/2007 | Gant et al. | |
| 2007/0197695 A1 | 8/2007 | Potyen et al. | |
| 2008/0103122 A1 | 5/2008 | Veltri | |

FOREIGN PATENT DOCUMENTS

| | | |
|---|---|---|
| WO | WO 95/26325 A2 | 10/1995 |
| WO | WO 2005118548 A1 * | 12/2005 |
| WO | WO 2007/105177 A1 | 9/2007 |
| WO | WO 2007/118651 A1 | 10/2007 |
| WO | WO 2009/079637 A1 | 6/2009 |

OTHER PUBLICATIONS

Written Opinion of PCT/US08/87477 (Form 237), completed Feb. 2008.*
Bailie, T. A., "The Use of Stable Isotopes in Pharmacological Research," *Pharmacological Reviews*, 33(2): 81-132 (1981).
Brisbare-Roch, C., et al., "Promotion of Sleep by Targeting the Orexin System in Rats, Dogs and Humans," *Nature Medicine*, 13(2), 150-155 (2007).
Browne, T. R., "Stable Isotope Techniques in Early Drug Development: An Economic Evaluation," *J. Clin. Pharmacol.*, 38: 213-220 (1998).
Cherrah, Y., et al., "Study of Deuterium Isotope Effects on Protein Binding by Gas Chromatography/Mass Spectrometry. Caffeine and Deuterated Isotopomers," *Biomedical and Environmental Mass Spectrometry*, 14: 653-657 (1987).
Dyck, L. E., et al., "Effects of Deuterium Substitution on the Catabolism of β-Phenylethylamine: An In Vivo Study," *Journal of Neurochemistry*, 46(2): 399-404 (1986).
Fisher, M.B. et al., "The Complexities Inherent in Attempts to Decrease Drug Clearance by Blocking Sites of CYP-Mediated Metabolism," *Curr. Opin. Drug Discov. Devel.*, 9(1):101-109 (2006).
Foster, A. B., "Deuterium Isotope Effects in Studies of Drug Metabolism," *Trends in Pharmacological Sciences*, 5: 524-527 (1984).
Foster, A. B., "Deuterium Isotope Effects in the Metabolism of Drugs and Xenobiotics: Implications for Drug Design," *Advances in Drug Research*, 14: 1-40 (1985).
Gouyette, A., "Synthesis of Deuterium-labelled Elliptinium and its Use in Metabolic Studies," *Biomedical and Environmental Mass Spectrometry*, 15: 243-247 (1988).
Haskins, N. J., "The Application of Stable Isotopes in Biomedical Research," *Biomedical Mass Spectrometry*, 9(7): 269-277 (1982).
Honma S., et al., "The Metabolism of Roxatidine Acetate Hydrochloride," *Drug Metabolism and Disposition*, 15(4): 551-559 (1987).
Kushner, D.J. et al., "Pharmacological Uses and Perspectives of Heavy Water and Deuterated Compounds," *Can. J. Physiol. Pharmacol.*, 77:79-88 (1999).
Pieniaszek, H. J., et al., "Moricizine Bioavailability via Simultaneous, Dual, Stable Isotope Administration: Bioequivalence Implications," *J. Clin. Pharmacol*, 39: 817-825 (1999).
Tonn G. R., et al., "Simultaneous Analysis of Diphenhydramine and a Stable Isotope Analog ($^2H_{10}$) Diphenhydramine Using Capillary Gas Chromatography with Mass Selective Detection in Biological Fluids from Chronically Instrumented Pregnant Ewes," *Biological Mass Spectrometry*, 22: 633-642 (1993).
Wolen, R. L., "The Application of Stable Isotopes to Studies of Drug Bioavailability and Bioequivalence," *J. Clin. Pharmacol.*, 26: 419-424 (1986).
Notification of Transmittal of the International Search Report (ISR) and the Written Opinion (WO) of the International Searching Authority, or the Declaration; International Application No. PCT/US08/087477, Date of Mailing Feb. 25, 2009.
Notification Concerning Transmittal of International Preliminary Report on Patentability, International Application No. PCT/US2008/087477, Date of Mailing Jul. 1, 2010.

* cited by examiner

*Primary Examiner* — Zinna Northington David
(74) *Attorney, Agent, or Firm* — Hamilton, Brook, Smith & Reynolds, P.C.

(57) ABSTRACT

This invention relates to novel tetrahydroisoquinoline derivatives, their derivatives, pharmaceutically acceptable salts thereof. This invention also provides compositions comprising a compound of this invention and the use of such compositions in methods of treating diseases and conditions that are beneficially treated by administering a dual OX-1/OX-2 orexin antagonist.

19 Claims, No Drawings

TETRAHYDROISOQUINOLINE DERIVATIVES

CROSS REFERENCE TO RELATED APPLICATIONS

This application claims priority to U.S. application Ser No. 61/014,635, filed Dec. 18, 2007, which is incorporated herein by reference in its entirety.

FIELD OF THE INVENTION

This invention relates to novel tetrahydroisoquinoline derivatives, their derivatives, pharmaceutically acceptable salts thereof. This invention also provides compositions comprising a compound of this invention and the use of such compositions in methods of treating diseases and conditions that are beneficially treated by administering a dual OX-1/OX-2 orexin antagonist.

BACKGROUND OF THE INVENTION

Almorexant, also known as 2(R)-(6,7-dimethoxy-1(S)-(2-(4-(trifluoromethyl)phenyl)ethyl)-1,2,3,4-tetrahydroisoquinolin-2-yl)-N-methyl-2-phenylacetamide, acts as a dual OX-1/OX-2 receptor antagonist. The neuropeptide hormones, orexin-1 and orexin-2 (OX-1, OX-2), also known as orexin A and B, or hypocretin-1 and -2, are produced in the hypothalamus and play an important role in the sleep-wake cycle. Blockade of OX-1 and OX-2 receptors has been shown to induce somnolence. (Brisbare-Roch, C. et al., *Nat. Med.*, February 2007, 13(2):150).

Almorexant is currently undergoing clinical trials for the treatment of insomnia.

Despite the beneficial activities of almorexant, there is a continuing need for new compounds to treat insomnia.

SUMMARY OF THE INVENTION

The invention provides a compound of formula I:

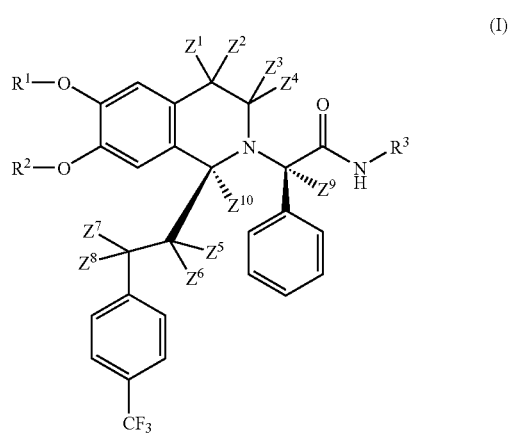

or a pharmaceutically acceptable salt thereof, wherein each Z is independently selected from hydrogen and deuterium, each R is independently selected from $CD_3$, $CD_2H$, $CDH_2$, and $CH_3$, and when each R is $CH_3$, at least one Z is deuterium. In one embodiment of the invention, each R is independently selected from $CD_3$, and $CH_3$. In another embodiment, $R^1$ and $R^2$ are the same. In other embodiments, $Z^1$ and $Z^2$ are the same, and/or $Z^3$ and $Z^4$ are the same; $Z^5$ and $Z^6$; and/or $Z^7$ and $Z^8$ are the same.

Specific examples of compounds of Formula I are shown in Table 1 below.

TABLE 1

| Compound | $R^1$ | $R^2$ | $R^3$ | $Z^1$ | $Z^2$ | $Z^3$ | $Z^4$ | $Z^5$ | $Z^6$ | $Z^7$ | $Z^8$ | $Z^9$ | $Z^{10}$ |
|---|---|---|---|---|---|---|---|---|---|---|---|---|---|
| 100 | $CD_3$ | $CD_3$ | $CD_3$ | D | D | D | D | D | D | D | D | D | D |
| 101 | $CD_3$ | $CD_3$ | $CD_3$ | H | H | H | H | H | H | H | H | H | H |
| 102 | $CD_3$ | $CD_3$ | $CD_3$ | D | D | H | H | H | H | D | D | D | D |
| 103 | $CD_3$ | $CD_3$ | $CD_3$ | H | H | H | H | D | D | D | D | H | D |
| 104 | $CD_3$ | $CD_3$ | $CD_3$ | H | H | H | H | D | D | D | D | H | H |
| 105 | $CD_3$ | $CD_3$ | $CD_3$ | D | D | D | D | H | H | H | H | H | H |
| 106 | $CD_3$ | $CD_3$ | $CD_3$ | H | H | H | H | H | H | H | H | D | D |
| 107 | $CD_3$ | $CD_3$ | $CD_3$ | H | H | H | H | H | H | H | H | D | H |
| 108 | $CD_3$ | $CD_3$ | $CH_3$ | D | D | D | D | D | D | D | D | D | D |
| 109 | $CD_3$ | $CD_3$ | $CH_3$ | H | H | H | H | H | H | H | H | H | H |
| 110 | $CD_3$ | $CD_3$ | $CH_3$ | D | D | H | H | H | H | D | D | D | D |
| 111 | $CD_3$ | $CD_3$ | $CH_3$ | H | H | H | H | D | D | D | D | H | D |
| 112 | $CD_3$ | $CD_3$ | $CH_3$ | H | H | H | H | D | D | D | D | H | H |
| 113 | $CD_3$ | $CD_3$ | $CH_3$ | D | D | D | D | H | H | H | H | H | H |
| 114 | $CD_3$ | $CD_3$ | $CH_3$ | H | H | H | H | H | H | H | H | D | D |
| 115 | $CD_3$ | $CD_3$ | $CH_3$ | H | H | H | H | H | H | H | H | D | H |
| 116 | $CH_3$ | $CH_3$ | $CD_3$ | D | D | D | D | D | D | D | D | D | D |
| 117 | $CH_3$ | $CH_3$ | $CD_3$ | H | H | H | H | H | H | H | H | H | H |
| 118 | $CH_3$ | $CH_3$ | $CD_3$ | D | D | H | H | H | H | D | D | D | D |
| 119 | $CH_3$ | $CH_3$ | $CD_3$ | H | H | H | H | D | D | D | D | H | D |
| 120 | $CH_3$ | $CH_3$ | $CD_3$ | H | H | H | H | D | D | D | D | H | H |
| 121 | $CH_3$ | $CH_3$ | $CD_3$ | D | D | D | D | H | H | H | H | H | H |
| 122 | $CH_3$ | $CH_3$ | $CD_3$ | H | H | H | H | H | H | H | H | D | D |
| 123 | $CH_3$ | $CH_3$ | $CD_3$ | H | H | H | H | H | H | H | H | D | H |

According to the invention, in compounds of formula I, any atom not designated as deuterium can be present at its natural isotopic abundance.

The invention further provides a pyrogen-free pharmaceutical composition comprising a compound of formula I and an acceptable carrier. In such a composition formulated for pharmaceutical administration, the carrier is a pharmaceutically acceptable carrier. In certain embodiments of the invention, the composition further comprises a second therapeutic agent useful in the treatment or prevention of a disease or a condition selected from an eating disorder, a sleep disorder and memory impairment. Examples of such a disease or condition include, but are not limited to obesity, bulimia, anorexia nervosa, insomnia, narcolepsy, sleep apnea, jetlag syndrome, and short-, middle- or long-term memory impairment.

The invention provides a method of inhibiting the activity of OX-1 or OX-2 in a brain cell, comprising the step of contacting the cell with a compound of formula I.

The invention also provides a method of treating a patient suffering from, or susceptible to, a disease or condition selected from an eating disorder, a sleep disorder and memory impairment comprising the step of administering to the patient in need thereof a compound of formula I and a pharmaceutically acceptable carrier. Such methods include but are not limited to treatment for a disease or condition selected from obesity, bulimia, anorexia nervosa, insomnia, narcolepsy, sleep apnea, jetlag syndrome, and short-, middle- or long-term memory impairment.

According to the invention, a compound of formula I may be administered with a second therapeutic agent useful in the treatment or prevention of a disease or a condition selected from an eating disorder, a sleep disorder and memory impairment. The second therapeutic agent can be combined with the compound of formula I in a single composition for administration, or can be in a separate composition administered simultaneously or on a different schedule as the compound of formula I, and can be an agent useful in the treatment or prevention of obesity, bulimia, anorexia nervosa, insomnia, narcolepsy, sleep apnea, jetlag syndrome, or short-, middle- or long-term memory impairment.

The invention also provides methods for synthesis of deuterated compounds of formula I.

DETAILED DESCRIPTION OF THE INVENTION

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of almorexant will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X"% of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert", """, and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of formula I:

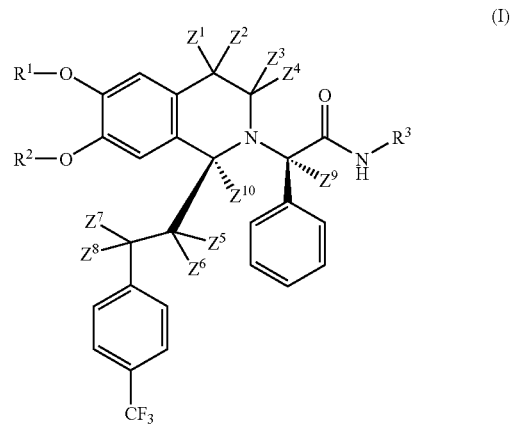

or a pharmaceutically acceptable salt thereof, wherein each Z is independently selected from hydrogen or deuterium, each R is independently selected from $CD_3$, $CD_2H$, $CDH_2$, and $CH_3$; and, when each R is $CH_3$, at least one Z is deuterium.

Other embodiments of a compound of formula I have one or more of the following features:
 a) $R^1$ and $R^2$ are the same;
 b) each R is independently selected from $CD_3$ and $CH_3$;
 c) $Z^1$ and $Z^2$ are the same;
 d) $Z^3$ and $Z^4$ are the same;
 e) $Z^5$ and $Z^6$ are the same; and
 f) $Z^7$ and $Z^8$ are the same.

Further embodiments have two or more features set forth in a) through f) above.

Another embodiment relates to compounds of formula I where $Z^1$, $Z^2$, $Z^3$, and $Z^4$ are the same. Another embodiment relates to compounds of formula I where $Z^5$, $Z^6$, $Z^7$, and $Z^8$ are the same.

Specific examples of compounds of formula I are shown in Table 1 below.

TABLE 1

| Compound | $R^1$ | $R^2$ | $R^3$ | $Z^1$ | $Z^2$ | $Z^3$ | $Z^4$ | $Z^5$ | $Z^6$ | $Z^7$ | $Z^8$ | $Z^9$ | $Z^{10}$ |
|---|---|---|---|---|---|---|---|---|---|---|---|---|---|
| 100 | $CD_3$ | $CD_3$ | $CD_3$ | D | D | D | D | D | D | D | D | D | D |
| 101 | $CD_3$ | $CD_3$ | $CD_3$ | H | H | H | H | H | H | H | H | H | H |
| 102 | $CD_3$ | $CD_3$ | $CD_3$ | D | D | H | H | D | D | D | D | D | D |
| 103 | $CD_3$ | $CD_3$ | $CD_3$ | H | H | H | H | D | D | D | D | H | D |
| 104 | $CD_3$ | $CD_3$ | $CD_3$ | H | H | H | H | D | D | D | D | H | H |
| 105 | $CD_3$ | $CD_3$ | $CD_3$ | D | D | D | D | H | H | H | H | H | H |
| 106 | $CD_3$ | $CD_3$ | $CD_3$ | H | H | H | H | H | H | H | H | D | D |
| 107 | $CD_3$ | $CD_3$ | $CD_3$ | H | H | H | H | H | H | H | H | D | H |

TABLE 1-continued

| Compound | R¹ | R² | R³ | Z¹ | Z² | Z³ | Z⁴ | Z⁵ | Z⁶ | Z⁷ | Z⁸ | Z⁹ | Z¹⁰ |
|---|---|---|---|---|---|---|---|---|---|---|---|---|---|
| 108 | CD₃ | CD₃ | CH₃ | D | D | D | D | D | D | D | D | D | D |
| 109 | CD₃ | CD₃ | CH₃ | H | H | H | H | H | H | H | H | H | H |
| 110 | CD₃ | CD₃ | CH₃ | D | D | H | H | H | H | D | D | D | D |
| 111 | CD₃ | CD₃ | CH₃ | H | H | H | H | D | D | D | D | H | D |
| 112 | CD₃ | CD₃ | CH₃ | H | H | H | H | D | D | D | D | H | H |
| 113 | CD₃ | CD₃ | CH₃ | D | D | D | D | H | H | H | H | H | H |
| 114 | CD₃ | CD₃ | CH₃ | H | H | H | H | H | H | H | H | D | D |
| 115 | CD₃ | CD₃ | CH₃ | H | H | H | H | H | H | H | H | D | H |
| 116 | CH₃ | CH₃ | CD₃ | D | D | D | D | D | D | D | D | D | D |
| 117 | CH₃ | CH₃ | CD₃ | H | H | H | H | H | H | H | H | H | H |
| 118 | CH₃ | CH₃ | CD₃ | D | D | H | H | H | H | D | D | D | D |
| 119 | CH₃ | CH₃ | CD₃ | H | H | H | H | D | D | D | D | H | D |
| 120 | CH₃ | CH₃ | CD₃ | H | H | H | H | D | D | D | D | H | H |
| 121 | CH₃ | CH₃ | CD₃ | D | D | D | D | H | H | H | H | H | H |
| 122 | CH₃ | CH₃ | CD₃ | H | H | H | H | H | H | H | H | D | D |
| 123 | CH₃ | CH₃ | CD₃ | H | H | H | H | H | H | H | H | D | H |

In another set of embodiments of the invention, any atom not designated as deuterium in any of the embodiments as set forth above is present at its natural isotopic abundance.

The synthesis of compounds of formula I can be readily achieved by synthetic chemists of ordinary skill. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in PCT publication WO 2005/118548. The compounds may be prepared as illustrated in the schemes shown below.

Compounds of the invention are orexin antagonists. The ability of the compounds to bind to and antagonize binding of orexins to human $OX_1$ and $OX_2$ receptors can be demonstrated by measuring binding to cloned receptors. See, for example, Smart, D et al., 2001, Br. J. Pharmacol., 132: 1179-82, which describes cloning and expression of human $OX_1$ and $OX_2$ receptors, and inhibition of binding of rhodamine green tagged orexin-A to $OX_1$, and Zhu, Y et al., 2003, J. Pharmacol. Sci., 92: 259-66, which describes expression of rat $OX_1$ and $OX_2$ receptors in BIM cells. Another way to confirm antagonism of $OX_1$ and $OX_2$ receptors by an orexin receptor antagonist is by measuring inhibition of receptor-mediated calcium responses. See, e.g., Smart et al., 2001.

Exemplary Synthesis

Scheme 1: General Route to Compounds of Formula I.

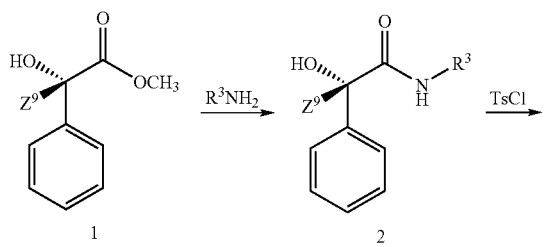

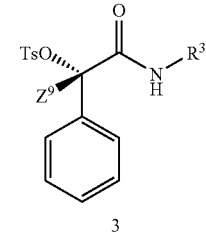

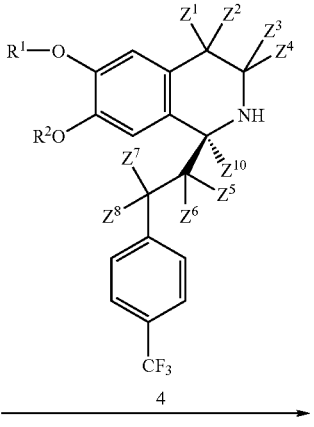

Formula I

Scheme 1 depicts a general route to preparing compounds of formula I. As described generally in the almorexant literature cited above, deuterated methyl (S)-mandelate 1 is treated with an appropriately-deuterated amine to afford amide 2. Activation of the hydroxyl group with p-toluenesulfonyl chloride, followed by displacement with intermediate 4, provides compounds of Formula I. For example, commercially-available methyl (S)-mandelate may be treated with commercially-available methyl-d₃-amine to ultimately produce compounds of Formula I wherein R³ is CD₃ and Z⁹ is H.

Scheme 2: Preparation of Ester 1b.

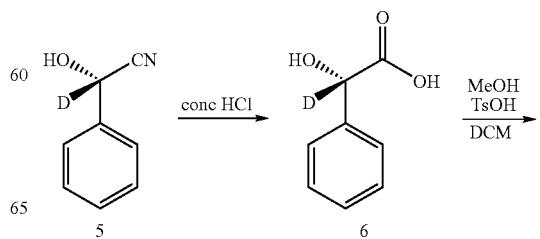

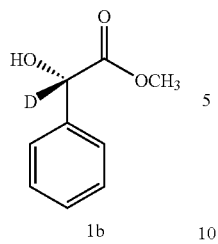

Scheme 2 depicts the preparation of deuterated ester 1b, which is a useful starting material for Scheme 1. (S)-2-hydroxy-2-phenyl-2-$d_1$-acetonitrile 5, which is synthesized from commercially-available benzaldehyde-α-$d_1$ and trimethylsilyl cyanide following the general procedure of Uang, B-J et al., Tetrahedron, 2004, 60(46): 10479-10486, is hydrolyzed stereoselectively using concentrated (conc) HCl to provide carboxylic acid 6 (see Effenberger, F et al., Tetrahedron Letters, 1990, 31(9): 1249-52.) Esterification with p-toluenesulfonic acid and methanol in dichloromethane (DCM), following the procedure of Kameyama, M et al., Journal of Organic Chemistry, 1987, 52(15): 3312-16, affords ester 1b.

Scheme 3: Preparation of Intermediate 4.

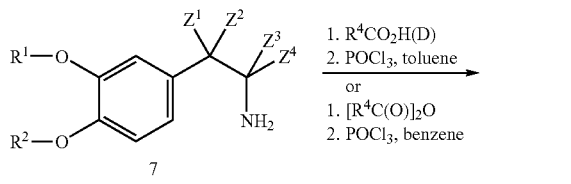

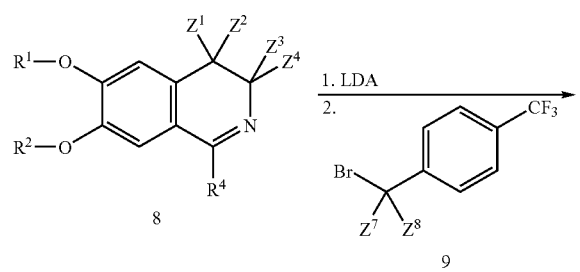

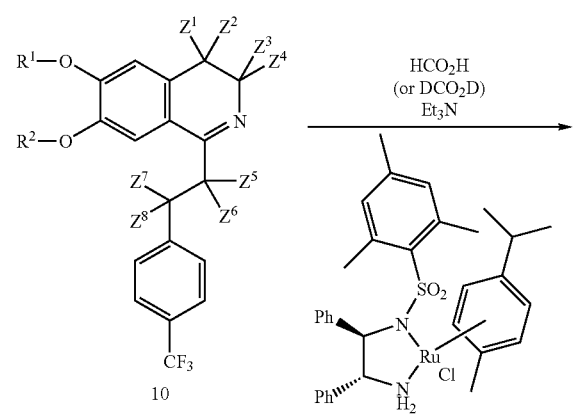

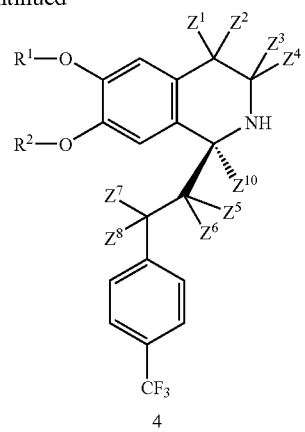

Scheme 3 depicts the preparation of intermediate 4, which is a useful intermediate for Scheme 1. Appropriately deuterated amine 7 is cyclized to provide bicycle 8 via treatment with appropriately-deuterated acetic acid ($R^4$=$CH_3$, $CDH_2$, $CD_2H$, or $CD_3$), followed by phosphorus oxychloride in toluene (see Gibson, H W et al., Journal of Organic Chemistry, 2007, 72(15): 5759-5770.) Alternatively, amine 7 may be cyclized via treatment with appropriately-deuterated acetic anhydride ($R^4$=$CH_3$, $CDH_2$, $CD_2H$, or $CD_3$), followed by phosphorus oxychloride in benzene (see Cui, W et al., Phytochemistry (Elsevier), 2006, 67(1): 70-79.) Following the almorexant literature cited above, bicycle 8 is treated with LDA, followed by appropriately-deuterated bromide 9, to yield imine 10. Stereoselective transfer hydrogenation of the imine with formic acid (or deuterated formic acid) and triethylamine in the presence of a Noyori ruthenium chiral catalyst affords intermediate 4.

Scheme 4: Alternate Preparation of Intermediate 10.

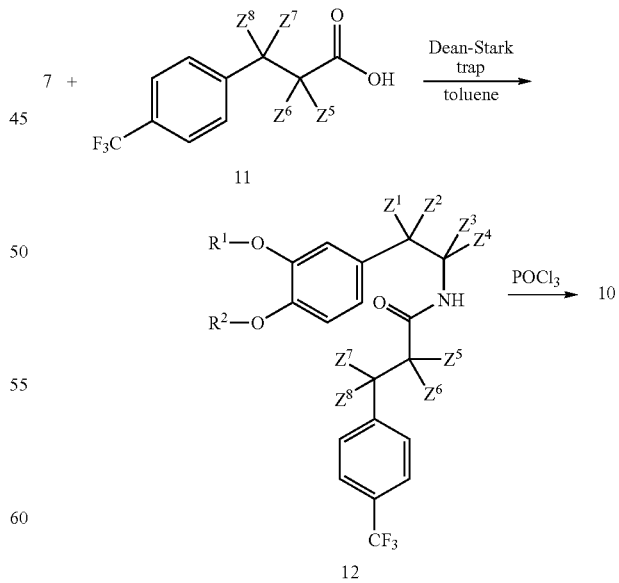

Scheme 4 depicts an alternate preparation of intermediate 10, following the almorexant literature cited above. Deuterated amine 7 is condensed with appropriately-deuterated carboxylic acid 11 in refluxing toluene with removal of water to provide amide 12. Treatment with phosphorus oxychloride affords intermediate 10.

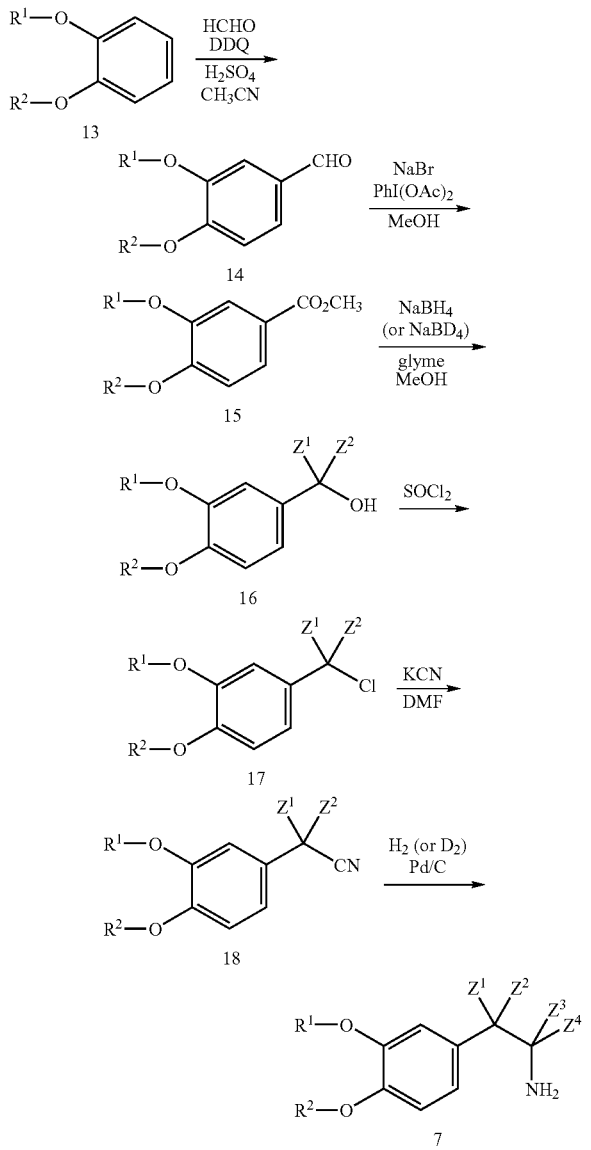

Scheme 5 depicts the preparation of amine 7, which is a useful intermediate for Scheme 3 and Scheme 4. Deuterated dimethoxybenzene 13 is formylated and oxidized in one step (see Branytska, O et al., Synlett, 2004, (9): 1575-1576) to provide aldehyde 14. Treatment of the aldehyde with sodium bromide and iodosobenzene diacetate and methanol affords the methyl ester 15 (see Karade, N N et al., Journal of Chemical Research, 2005, (4): 274-276). Ester reduction with sodium borohydride or sodium borodeuteride in methanolic glyme (see Zanka, A et al., Synlett 1999, (10): 1636-1638) provides alcohol 16. Chlorination of the alcohol with thionyl chloride yields chloride 17 (see Howell, S J et al., Tetrahedron, 2001, 57(23): 4945-4954). Displacement of the chloride with potassium cyanide in DMF affords nitrile 18 (see Theodore, L J et al., Journal of Labelled Compounds and Radiopharmaceuticals, 1989, 27(5): 491-501). Reduction of the nitrile with either hydrogen or deuterium in the presence of palladium on carbon (see Vincze, Z et al., Synthesis, 2006 (8): 1375-1385) affords the desired amine 7. For example, commercially-available 1,2-di(methoxy-$d_3$)-benzene

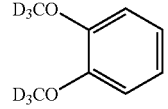

may be used as compound 13 in Scheme 5 to provide compounds of Formula I wherein $R^1$ and $R^2$ are both $CD_3$.

In another example, commercially-available methyl 3,4-dimethoxybenzoate

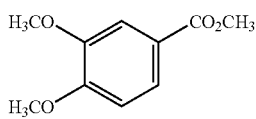

may be used as compound 15 in Scheme 5 to provide compounds of Formula I wherein $R^1$ and $R^2$ are both $CH_3$.

Scheme 6. Preparation of Carboxylic Acid 11.

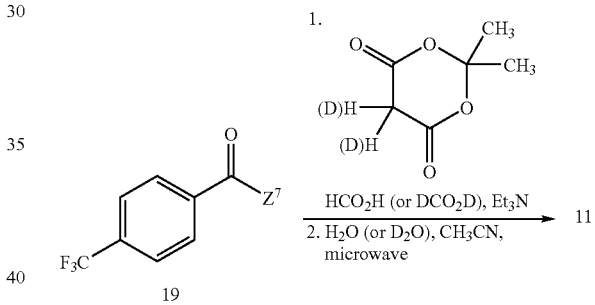

Scheme 6 depicts the preparation of carboxylic acid 11, which is a useful intermediate for Scheme 4. Following the method of Sharma, A K et al., Tetrahedron, 2007, 63(2): 389-395, appropriately-deuterated aldehyde 19 is treated with appropriately-deuterated Meldrum's Acid, appropriately-deuterated formic acid, and triethylamine, followed by microwave heating in acetonitrile and appropriately-deuterated water to yield carboxylic acid 11. For example, known 4-(trifluoromethyl)-benzaldehyde-formyl-d

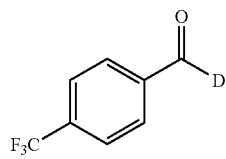

(see Yamada, Issaku, Noyori, Ryoji, Organic Letters, 2000, 2(22): 3425-3427), may be used as compound 19 in Scheme 6 along with known deuterated Meldrum's Acid (see Abramovitch, RA, Canadian Journal of Chemistry, 1959, 37: 361-365) to ultimately provide compounds of Formula I wherein $Z^5$, $Z^6$, $Z^7$ and $Z^8$ are all deuterium.

Scheme 7. Alternate Preparation of Carboxylic Acid 11.

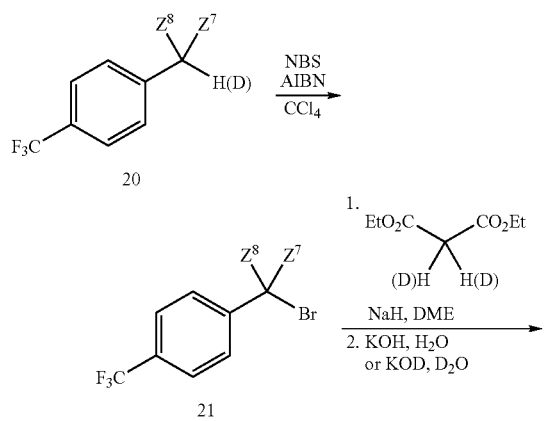

Scheme 7 depicts an alternate preparation of carboxylic acid 11, which is a useful intermediate for Scheme 4. Following the method of Reinhard, E J et al., Journal of Medicinal Chemistry, 2003, 46(11): 2152-2168, appropriately-deuterated toluene derivative 20 is brominated with NBS and AIBN to afford bromide 21. Treatment with sodium hydride and appropriately-deuterated diethyl malonate in DME, followed by hydrolysis of the resulting ester with appropriately-deuterated potassium hydroxide provides carboxylic acid 11 according to the general methods of Musso, D L et al., J. Med. Chem., 2003, 46: 409-416. For example, known 1-(methyl-d$_3$)-4-(trifluoromethyl)-benzene

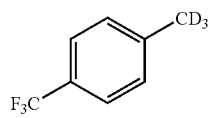

(see Holland, H L et al., Journal of the Chemical Society, Perkin Transactions 2: Physical Organic Chemistry (1972-1999), 1990, 10: 1651-5), may be used as compound 20 in Scheme 7 to ultimately provide compounds of Formula I wherein $Z^7$ and $Z^8$ are both deuterium. In another example, commercially-available 4-(trifluoromethyl)benzyl bromide may be used as compound 21 in Scheme 7 along with commercially-available diethyl malonate-d$_2$

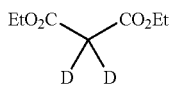

to ultimately provide compounds of Formula I wherein $Z^5$ and $Z^6$ are both deuterium.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art. Additional methods of synthesizing compounds of formula I and their synthetic precursors, including those within routes not explicitly shown in schemes herein, are within the means of chemists of ordinary skill in the art. Methods for optimizing reaction conditions and, if necessary, minimizing competing by-products, are known in the art. In addition to the synthetic references cited herein, reaction schemes and protocols may be determined by the skilled artisan by use of commercially available structure-searchable database software, for instance, SciFinder® (CAS division of the American Chemical Society), STN® (CAS division of the American Chemical Society), CrossFire Beilstein® (Elsevier MDL), or internet search engines such as Google® or keyword databases such as the United States Patent and Trademark Office text database.

The methods described herein may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis*, 3$^{rd}$ Ed., John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of formula I (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations Enhancing the Bioavailability of Poorly Water-Soluble Drugs (Drugs and the Pharmaceutical Sciences)," David J. Hauss, ed. Informa Health-care, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 2006/0094744 and 2006/0079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as almorexant.

Such agents include those indicated as being useful in the treatment or prevention of a disease or condition selected from eating disorders such as obesity, bulimia and anorexia nervosa, and sleep disorders including insomnia, narcolepsy, sleep apnea, and jetlag syndrome, and short-, middle- and/or long-term memory impairment.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50:219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from about 0.01 mg to about 10,000 mg per treatment. In a more specific embodiment the range is from about 0.1 mg to about 5,000 mg, or from about 0.2 mg to about 2,000 mg, or most specifically from about 1 mg to about 1,000 mg per treatment. Treatment typically is administered once daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for almorexant.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

In one embodiment of the invention, when a second therapeutic agent is administered to a subject, the effective amount of the compound of this invention is less than its effective amount would be where the second therapeutic agent is not administered. In another embodiment, the effective amount of the second therapeutic agent is less than its effective amount would be where a compound of this invention is not administered. This has the advantage of minimizing toxic side effects of either the second therapeutic agent of a compound of this invention. Other potential advantages (including without limitation improved dosing regimens and/or reduced drug cost) will be apparent to those of skill in the art.

Methods of Treatment

In another embodiment, the invention provides a method of blocking the activity of OX-1 and OX-2 in a brain cell, comprising contacting such a cell with one or more compounds of formula I herein.

According to another embodiment, the invention provides a method of treating a patient suffering from, or susceptible to, a disease that is beneficially treated by almorexant comprising the step of administering to said patient an effective amount of a compound or a composition of this invention. Such diseases are well known in the art and are disclosed in, but not limited to the following patents and published applications: WO 2005/118548, and WO 2007/105177. Such diseases include, but are not limited to, eating disorders such as obesity, bulimia and anorexia nervosa, and sleep disorders including insomnia, narcolepsy, sleep apnea, and jetlag syndrome, and short-, middle- and/or long-term memory impairment.

In one particular embodiment, the method of this invention is used to treat a patient suffering from or susceptible to insomnia.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with almorexant. The choice of second therapeutic agent is also dependent upon the particular disease or condition to be treated. Examples of second therapeutic agents that may be employed in the methods of this invention include any described for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of formula I for use in the treatment or prevention in a patient of a disease, disorder or symptom thereof delineated herein.

Pharmaceutical Kits

The present invention also provides kits for use to treat insomnia. These kits comprise (a) a pharmaceutical composition comprising a compound of formula I or a salt thereof, wherein said pharmaceutical composition is in a container; and (b) instructions describing a method of using the pharmaceutical composition to treat insomnia.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of N-((1R,2R)-2-Amino-1,2-diphenylethyl)-2,4,6-trimethylbenzenesulfonamide (32)

Intermediate 32 was prepared as outlined in Scheme 8 below. Details of the synthesis are set forth below. Scheme 8. Preparation of Intermediate 32.

Scheme 8. Synthesis of Intermediate 32.

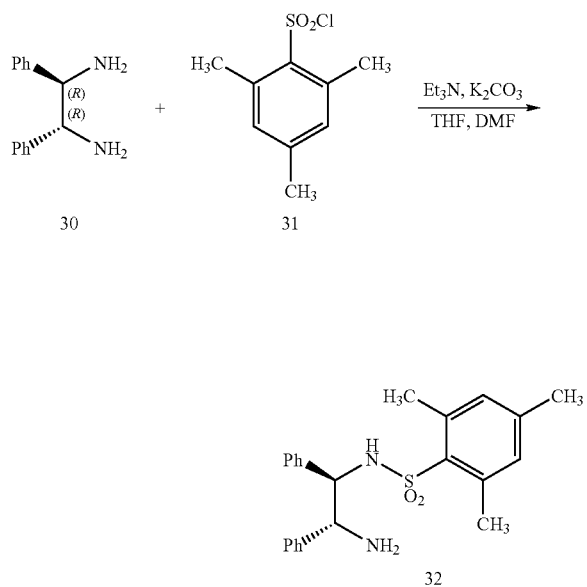

Synthesis of N-((1R,2R)-2-Amino-1,2-diphenylethyl)-2,4,6-trimethylbenzenesulfonamide (32)

A solution of 2,4,6-trimethylbenzene-1-sulfonyl chloride 31 (1.54 g, 7.06 mmol, 0.99 eq) in tetrahydrofuran (75 mL) was added drop-wise at 0° C. over 70 minutes (min) to a suspension of (1R,2R)-1,2-diphenylethane-1,2-diamine 30 (1.5 g, 7.08 mmol, 1.0 eq), triethylamine (2.04 g, 2.8 mL, 2.02 mmol, 0.28 eq) and powdered potassium carbonate (1.60 g, 11.59 mmol, 1.64 eq) in a mixture of tetrahydrofuran (60 mL) and N,N-dimethylformamide (15 mL). When addition was complete the suspension was stirred at 0° C. for 3 hours (h). The reaction mixture was concentrated under reduced pressure to remove most of the tetrahydrofuran. The residual oily solid was partitioned between water (100 mL) and 3:1 ethyl acetate/heptanes. The organic phase was diluted with heptanes (50 mL) and the solution washed with water (3×100 mL) followed by brine (100 mL). The organic solution was dried over sodium sulfate, filtered and the filtrate concentrated under reduced pressure to give a pale yellow oil. The crude product was dissolved in a minimum volume of dichloromethane, adsorbed onto silica gel and dry-loaded on a column of silica gel (50 g) packed in 75% ethyl acetate/heptanes. The column was eluted with 75% ethyl acetate/heptanes (300 mL) and ethyl acetate (300 mL). Product-containing fractions were concentrated under reduced pressure to give a slightly gummy solid that was triturated with hexanes containing a small amount of methyl t-butyl ether, filtered, washed with hexanes and dried to give 1.90 g of 32 as a white solid.

Example 2

Synthesis of (S)-2-((Methyl-d₃)amino)-2-oxo-1-phenylethyl 4-methylbenzenesulfonate (35)

Intermediate 35 was prepared as outlined in Scheme 9 below and as described below.

Scheme 9. Preparation of Intermediate 35.

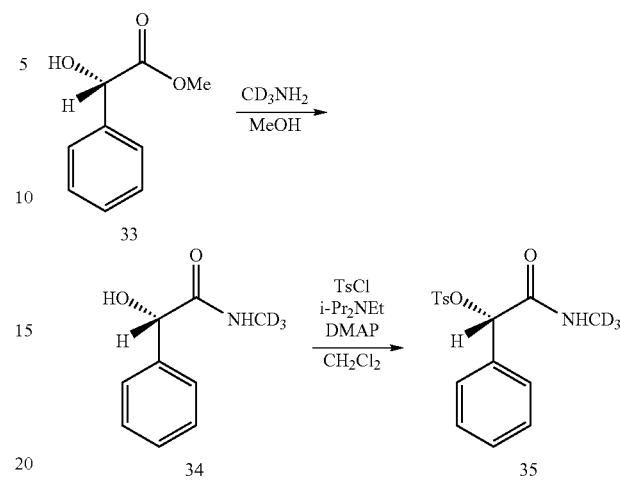

Synthesis of (S)-2-Hydroxy-N-(methyl-d₃)-2-phenylacetamide (34). A solution of methyl (S)-(+)-mandelate 33 (5.00 g, 30.12 mmol, 1.0 eq) in methanol (100 mL) was cooled to approximately −9° C. in an ice/salt bath and methylamine-d₃ (5.0 g, 147 mmol, 4.9 eq) (CDN Isotopes, 99.6 atom % D) was condensed into the solution using a dry-ice condenser. The reaction mixture was allowed to warm to room temperature (rt) and stirred over a weekend. The solution was concentrated under reduced pressure to a volume of approximately 25 mL. The mixture was diluted with toluene (75 mL) and concentrated under reduced pressure to give a white crystalline solid. The solid was dried under vacuum at rt to give 5.13 g (101%) of 34 as a white solid.

Synthesis of (S)-2-((Methyl-d₃)-amino)-2-oxo-1-phenylethyl 4-methylbenzenesulfonate (35). N,N-Diisopropylethylamine (DIPEA) (3.41 g, 4.6 mL, 26.4 mmol, 1.05 eq) followed by 4-dimethylaminopyridine (DMAP) (0.31 g, 2.5 mmol, 10 mol %) was added to a solution of 34 (4.23 g, 25.2 mmol, 1.0 eq) in dichloromethane (100 mL). p-Toluenesulfonyl chloride (TsCl) (5.26 g, 27.7 mmol, 1.1 eq) was added portion-wise at rt and the mixture was stirred overnight at rt. The yellow reaction mixture was diluted with dichloromethane (150 mL) and the solution was washed sequentially with 1N hydrochloric acid (100 mL) and saturated sodium bicarbonate solution (100 mL). The organic solution was dried over sodium sulfate, filtered and the filtrate concentrated under reduced pressure to give a tan solid. The crude product was dissolved in a minimum volume of dichloromethane, adsorbed onto silica gel and dry-loaded on a column of silica gel (125 g) packed in heptanes. The column was eluted with heptanes (750 mL), 10% ethyl acetate/heptanes (1 L), 25% ethyl acetate/heptanes (1 L), 33% ethyl acetate/heptanes (900 mL), 40% ethyl acetate/heptanes (3 L), and 50% ethyl acetate/heptanes (1 L). Product-containing fractions were concentrated under reduced pressure to give 5.14 g (63%) of 35 as a white solid.

Example 3

Synthesis of (S)-2-(Methylamino)-2-oxo-1-phenylethyl 4-methylbenzenesulfonate (38)

Intermediate 38 was prepared as outlined in Scheme 10 below and as described below.

Scheme 10. Preparation of Intermediate 38.

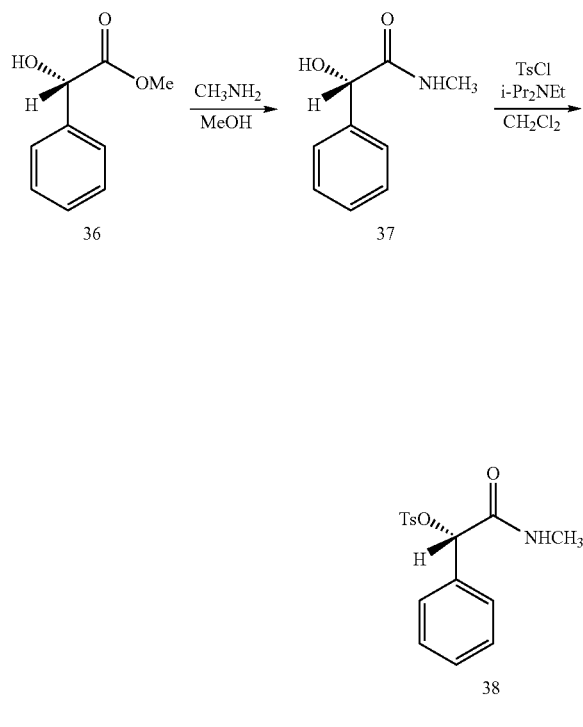

Scheme 11. Preparation of Compound 101.

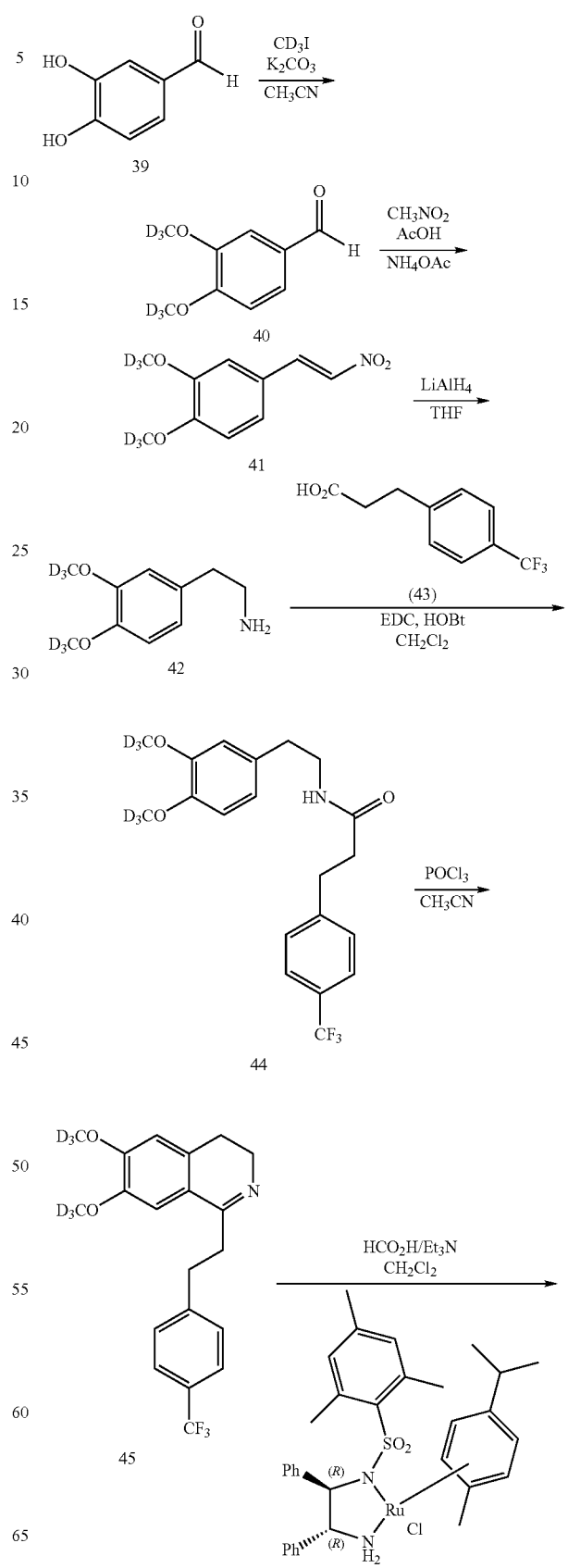

Synthesis of (S)-2-Hydroxy-N-methyl-2-phenylacetamide (37). Methyl (S)-(+)-mandelate 36 (4.60 g, 27.7 mmol, 1.0 eq) was added to a 2M solution of methylamine in methanol, (70 mL, 140 mmol, 5.05 eq) and the mixture was stirred at rt for 24 h. The mixture was concentrated under reduced pressure to a semi-solid. Residual methanol was co-evaporated with toluene (2×50 mL) followed by 1:1 toluene/heptanes (50 mL) to give a white crystalline solid. The solid was triturated with heptanes (50 mL), filtered and dried to give 4.35 g (95%) of 37 as a white solid.

Synthesis of (S)-2-(Methylamino)-2-oxo-1-phenylethyl 4-methylbenzenesulfonate (38). TsCl (4.75 g, 25 mmol, 1.0 eq) was added portion-wise at rt to a solution of 37 (4.13 g, 25 mmol, 1.0 eq) and DIPEA (3.22 g, 4.4 mL, 25 mmol, 1.0 eq) in dichloromethane (100 mL). The reaction mixture was stirred at rt for 5 h, then was concentrated under reduced pressure to give an oil. The crude oil was dissolved in ethyl acetate (150 mL), and the solution was washed sequentially with water (100 mL), saturated sodium bicarbonate solution (2×75 mL) and brine (75 mL). The organic solution was dried over sodium sulfate and filtered. The filtrate was concentrated under reduced pressure to near dryness. The solid was triturated with methyl t-butyl ether (100 mL), filtered and dried to give 4.89 g (61%) of 38 as a white solid.

Example 4

Synthesis of (R)-2-((S)-6,7-Di(methoxy-$d_3$)-1-(4-(trifluoromethyl)phenethyl)-3,4-dihydroisoquinolin-2(1H)-yl)-N-(methyl-$d_3$)-2-phenylacetamide hydrochloride (101)

Compound 101 was prepared as outlined in Scheme 11 below. Details of the synthesis are as follows.

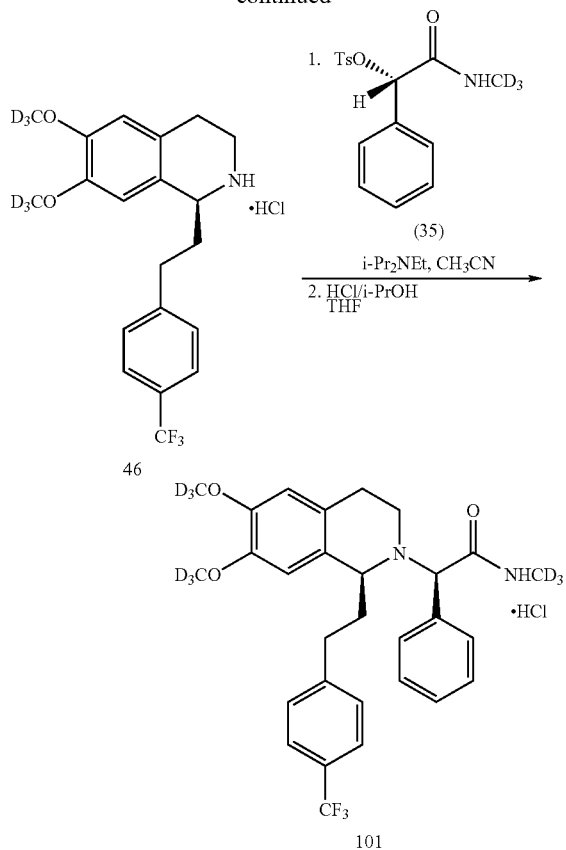

Synthesis of 3,4-Di(methoxy-d₃)benzaldehyde (40). Iodomethane-d₃ (21.75 g, 9.3 mL, 150 mmol, 3.16 eq) (Cambridge Isotopes, 99.5 atom % D) was added slowly to a yellow suspension of 3,4-dihydroxybenzaldehyde 39 (6.56 g, 47.5 mmol, 1.0 eq) and powdered potassium carbonate (20.70 g, 150 mmol, 3.0 eq) in acetonitrile (150 mL). A small increase in reaction temperature (1-2° C.) was observed. The mixture was heated at approximately 45° C. for 8 h, cooled to rt and stirred over a weekend. The tan suspension was filtered, the solids were washed with ethyl acetate (150 mL) and the filtrate concentrated under reduced pressure. The residual oily solid was partitioned between 3:2 ethyl acetate/heptanes (250 mL) and water (100 mL). The organic phase was washed with 10% aqueous sodium carbonate solution (100 mL), dried over sodium sulfate, filtered and the filtrate concentrated under reduced pressure to give 7.92 g (97%) of 40 as an oil which, upon seeding, slowly crystallized as a tan solid.

Synthesis of (E)-1,2-Di(methoxy-d₃)-4-(2-nitrovinyl)benzene (41). A mixture of 40 (7.92 g, 46 mmol, 1.0 eq), nitromethane (6.46 g, 5.7 mL, 106 mmol, 2.3 eq), ammonium acetate (4.61 g, 60 mmol, 1.3 eq) and acetic acid (40 mL) was heated at reflux for 5 h. Upon heating the reaction mixture turned yellow, then brown. The mixture was cooled to rt (a suspension formed) and stirred overnight. The suspension was cooled in an ice/water bath and diluted with 1:1 ethanol/water (100 mL). The solid was filtered and washed with 1:1 ethanol/water (100 mL). After drying on the filter for 15 min, the solid was washed with 1:1 ethanol/heptanes (100 mL) and dried to give 5.90 g (60%) of 41 as a yellow solid.

Synthesis of 3,4-Di(methoxy-d₃)phenethylamine (42). A solution of 41 (5.81 g, 27 mmol, 1.0 eq) in tetrahydrofuran (125 mL) was added dropwise to a 1M solution of lithium aluminum hydride in tetrahydrofuran (58 mL, 58 mmol, 2.15 eq) cooled in an ice/water bath, keeping the temperature at 10-15° C. during the addition. The resulting yellow-orange solution was allowed to warm to rt during which time a light suspension formed. The mixture was heated at reflux with the suspension initially becoming more viscous, then thinning. The color lightened to a creamy yellow color. After 3.5 h at reflux the mixture was cooled to rt and then to approximately 18° C. Water (2.2 mL) was added cautiously dropwise via syringe, followed by 15% aqueous sodium hydroxide (2.2 mL) and water (6.6 mL), keeping the internal temperature at 18-20° C. during the additions. The suspension was stirred 0.5 h then filtered through a pad of Celite, washing the pad with tetrahydrofuran (175 mL). The filtrate was concentrated under reduced pressure to give 4.82 g (95%) of crude 42 that was used without further purification.

Synthesis of N-(3,4-Di(methoxy-d₃)phenethyl)-3-(4-(trifluoromethyl)phenyl)propanamide (44). EDC (5.42 g, 28.3 mmol, 1.1 eq) was added to a suspension of 43 (5.62 g, 25.8 mmol, 1.0 eq) and 1-hydroxybenzotriazole (HOBt) (3.48 g, 25.8 mmol, 1.0 eq) in dichloromethane (250 mL). The mixture was stirred at rt for 20 min, giving a clear colorless solution. A solution of crude 42 (4.82 g, 25.8 mmol, 1.0 eq) in dichloromethane (25 mL) was added slowly with a small increase in reaction temperature from 22° C. to 25° C. The yellow solution was stirred at rt for 3.5 h, then washed with 1N hydrochloric acid (150 mL) followed by 0.5 N sodium hydroxide. The organic phase was dried over sodium sulfate, filtered and the filtrate concentrated under reduced pressure to give a tan solid. The crude product was dissolved in a minimum volume of dichloromethane, adsorbed onto silica gel and dry-loaded on a column of silica gel (125 g) packed in 10% ethyl acetate/toluene. The column was eluted with 10% ethyl acetate/toluene (1 L), 25% ethyl acetate/toluene (1 L), 33% ethyl acetate/toluene (900 mL) and 40% ethyl acetate/toluene. Product-containing fractions were concentrated under reduced pressure to give a yellowish white solid. The solid was triturated with heptanes (75 mL), filtered and dried to give 6.53 g (66%) of 44.

Synthesis of 6,7-Di(methoxy-d₃)-1-(4-(trifluoromethyl)phenethyl)-3,4-dihydroisoquinoline (45). Phosphorous oxychloride (7.08 g, 4.3 mL, 46.0 mmol, 2.2 eq) was added to a suspension of 44 (8.09 g, 20.9 mmol, 1.0 eq) in acetonitrile (150 mL). The mixture was heated at reflux giving a dark brown solution. After 2.75 h at reflux, the mixture was cooled to rt and stirred overnight. The mixture was concentrated under reduced pressure to give a dark brown viscous oil. Methanol was added very slowly to the oil and the solution was re-concentrated under reduced pressure. Water (150 mL) was added to the residue and the resulting suspension was adjusted to pH 9-10 with 1N sodium hydroxide then extracted with ethyl acetate (1×250 mL, 1×100 mL). The combined organic solution was washed with brine (100 mL), then stirred 15 min with sodium sulfate and charcoal (0.5 g). The mixture was filtered through Celite, and the filtrate concentrated under reduced pressure to give 7.52 g (97%) of crude 45 as a light brown solid that was used without further purification.

Synthesis of (S)-6,7-Di(methoxy-d₃)-1-(4-(trifluoromethyl)phenethyl) -1,2,3,4-tetrahydro-isoquinoline hydrochloride (46). This reaction utilizes a known catalyst developed by R. Noyori, et al. (see J. Am. Chem. Soc., 1996, 118: 4916-4917). A mixture of dichloro(p-cymene)-ruthenium(II) dimer (89 mg, 0.145 mmol, 0.71 mol %), 32 (114 mg, 0.290 mmol, 1.4 mol %) and triethylamine (0.08 mL, 0.58 mmol, 2.9 mol %) in acetonitrile (4 mL) was heated at reflux for 1 h. The mixture was cooled to rt and added to a solution of crude 45 (7.50 g, 20.3 mmol, 1.0 eq) in dichloromethane (100 mL)

giving a yellow-brown solution. Formic acid-triethylamine, 5:2 complex, (6 mL) was added slowly via syringe. The reaction temperature increased from 22° C. to 25° C. and gas evolved after the addition. The reaction mixture was stirred at rt for 3.5 h then quenched by the very slow addition of saturated sodium bicarbonate solution (100 mL). The mixture was transferred to a separatory funnel, diluted with dichloromethane (100 mL) and saturated sodium bicarbonate solution (100 mL) and shaken to neutralize all remaining formic acid. The organic phase was separated and the aqueous phase extracted with dichloromethane (50 mL). The combined organic solution was dried over sodium sulfate, filtered and the filtrate concentrated under reduced pressure to give a brown oil. The oil was dissolved in isopropanol (100 mL) and an approximately 5M solution of hydrogen chloride in isopropanol (12 mL) was added slowly with a thick precipitate forming. The suspension was stirred overnight at rt, then was filtered and the solids were washed with isopropanol (25 mL) and partially dried under nitrogen. Crude 46 (hydrochloride salt) was dissolved in refluxing ethanol (225 mL), then the solution was cooled to rt and stirred overnight. The solid was filtered, washed with a small volume of ethanol and dried under nitrogen to give 5.31 g of 46. An additional 0.68 g was obtained from the mother liquor.

The two crops of the hydrochloride salt were combined and suspended in dichloromethane (150 mL) and saturated sodium bicarbonate solution (75 mL) was added slowly with stirring until a clear biphasic mixture developed and the aqueous layer remained at pH≧8. The organic phase was dried over sodium sulfate, filtered and the filtrate concentrated under reduced pressure to give a light tan oil. The oil was redissolved in dichloromethane (15 mL), the solution diluted with hexanes (50 mL) and the mixture concentrated under reduced pressure to give an oil that partially crystallized upon seeding. Hexanes (75 mL) were added to the oily solid and the mixture was concentrated under reduced pressure (bath temperature ≦25° C.) to give 5.46 g of 46 as an off-white solid. Chiral HPLC (Chiralcel OD column, isocratic elution with 90% hexanes/10% ethanol) showed the material to be only 92% ee.

The sample of 46 from above was dissolved in ethanol (60 mL) and an approximately 5M solution of hydrogen chloride in isopropanol (5 mL) was added slowly with a thick precipitate forming. The mixture was heated at reflux, and ethanol was added in 10 mL increments until a nearly clear solution developed (a total volume of approximately 170 mL of ethanol was used). The mixture was cooled to rt and stirred overnight. The suspension was cooled to 0° C., the solid was filtered, washed with a small volume of ethanol and dried under nitrogen to give 5.17 g of 46 as the hydrochloride salt. Chiral HPLC analysis (Chiralcel OD column, isocratic elution with 90% hexanes/10% ethanol) of the free-base of 46 showed the material to be >99% ee.

Synthesis of (R)-2-((S)-6,7-Di(methoxy-d$_3$)-1-(4-(trifluoromethyl)phenethyl)-3,4-dihydroisoquinolin-2(1H)-yl)-N-(methyl-d$_3$)-2-phenylacetamide hydrochloride (101). DIPEA (0.99 g, 1.3 mL, 7.65 mmol, 2.25 eq) was added to a suspension of 46 (hydrochloride salt) (1.38 g, 3.40 mmol, 1.0 eq) and 35 (1.20 g, 3.74 mmol, 1.1 eq) in acetonitrile (50 mL) and the mixture was heated at reflux for 31 h. The resultant mixture was cooled to rt and stirred overnight, then was concentrated under reduced pressure to a small volume. The remaining solution was partitioned between ethyl acetate (150 mL) and saturated sodium bicarbonate solution (100 mL). The organic phase was dried over sodium sulfate, filtered and the filtrate concentrated under reduced pressure to give a yellow oil. The crude product was dissolved in a minimum volume of dichloromethane, adsorbed onto silica gel and dry-loaded on a column of silica gel (75 g) packed in 33% ethyl acetate. The column was eluted with 33% ethyl acetate/heptanes (500 mL), 40% ethyl acetate/heptanes (500 mL), 50% ethyl acetate/heptanes (500 mL), and 60% ethyl acetate/heptanes (1 L). Product-containing fractions were concentrated under reduced pressure to give a gummy oil. The gummy oil was dissolved in ethanol (25 mL) and an approximately 5M solution of hydrogen chloride in isopropanol (2 mL) was added, but no precipitate formed. The mixture was concentrated under reduced pressure to give an oily gum that was redissolved in ethyl acetate (20 mL). After several minutes a precipitate began to form. The suspension was concentrated under reduced pressure to an off-white solid. The solid was suspended in ethyl acetate (50 mL) and the mixture heated at reflux until a clear solution developed (approximately 1.5 h). The solution was allowed to cool to rt and was stirred overnight. The solid was filtered, washed with a small volume of ethyl acetate and dried under nitrogen to give 0.48 g of 101 as a white solid. Chiral HPLC (Chiralcel OD column, isocratic elution with 95% hexanes/5% ethanol) of the free-base of 101 showed the material to be >99% ee. $^1$H-NMR (300 MHz, CDCl$_3$): δ 1.94-2.05 (m, 1H), 2.81-2.82 (m, 2H), 3.04-3.15 (m, 2H), 3.20-3.35 (m, 1H), 3.79-3.86 (m, 2H), 3.90-3.95 (m, 1H), 4.55 (d, J=10.2, 1H), 5.73 (s, 1H), 6.68 (s, 1H), 7.10 (d, J=7.9, 2H), 7.38-7.47 (m, 5H), 7.61-7.64 (m, 2H), 9.55 (s, 1H), 12.60-12.66 (m, 1H). $^{13}$C-NMR (75 MHz, CDCl$_3$): δ 21.63, 32.14, 35.65, 43.50, 59.46, 71.94, 109.52, 111.59, 121.04, 121.14, 125.61, 125.66, 128.95, 129.43, 129.72, 129.83, 130.62, 143.28, 148.59, 149.73, 164.96. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 305 nm): retention time: 6.30 min; 99.4% purity. MS (M+H): 522.3. Elemental Analysis (C$_{29}$H$_{23}$D$_9$ClF$_3$N$_2$O$_3$): Calculated: C=62.42, H=5.78, Cl=6.35, N=5.02, F=10.21. Found: C=62.31, H=5.79, Cl=6.26, N=5.00, F=10.42.

Example 5

Synthesis of (R)-2-((S)-6,7-Dimethoxy-1-(4-(trifluoromethyl)phenethyl)-3,4-dihydroisoquinolin-2(1H)-yl)-N-(methyl-d$_3$)-2-phenylacetamide hydrochloride (117)

Compound 117 was prepared using appropriately deuterated reagents as generally outlined in Scheme 11 above, beginning with the non-deuterated analog of intermediate 42. This intermediate will be set forth as 42a. All such designations using the letter "a" following a compound number are in reference to the analog as found in Scheme 11. Details of the synthesis are as follows.

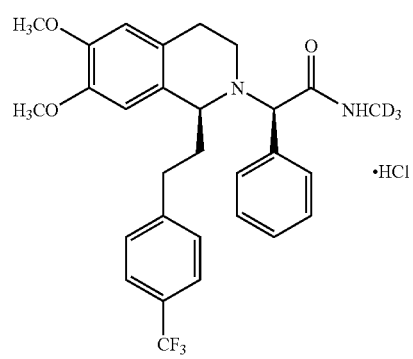

Synthesis of N-(3,4-Dimethoxyphenethyl)-3-(4-(trifluoromethyl)phenyl)propanamide (44a). 3,4-Dimethoxyphenethylamine 42a (3.62 g, 3.4 mL, 20 mmol, 1.0 eq) was added to a solution of 4-(trifluoromethyl)hydrocinnamic acid 43

(4.36 g, 20 mmol, 1.0 eq) in toluene (75 mL). After 5 min a thick suspension formed. The suspension was heated to reflux, giving a clear solution. The mixture was heated at reflux for 24 h using a Dean-Stark trap to remove water that was formed. The mixture was partially cooled, diluted with ethyl acetate (100 mL) and concentrated under reduced pressure to near dryness. The thick slurry was diluted with ethyl acetate (200 mL) and the solution washed sequentially with 1N hydrochloric acid (100 mL), aqueous sodium bicarbonate solution (200 mL), water (100 mL) and brine (100 mL). The organic solution was dried over sodium sulfate, filtered and the filtrate concentrated under reduced pressure. The solid was triturated with heptanes (50 mL), filtered and dried to give 5.37 g (70%) of 44a as a white, fluffy solid.

Synthesis of 6,7-Dimethoxy-1-(4-(trifluoromethyl)phenethyl)-3,4-dihydroisoquinoline (45a). Phosphorous oxychloride (4.77 g, 2.9 mL, 31.0 mmol, 2.2 eq) was added to a suspension of 44a (5.37 g, 14.1 mmol, 1.0 eq) in acetonitrile (100 mL) resulting in the formation of a clear solution. The mixture was heated at reflux for 3.5 h. The resulting yellow solution was cooled to rt and concentrated under reduced pressure to a thick yellow oil. The oil was dissolved in methanol (10 mL) and water (100 mL) was added slowly with stirring. After several minutes, a thick suspension formed. The mixture was made alkaline by the slow addition of saturated sodium bicarbonate solution, adding water (~100 mL) to facilitate stirring. The thick white suspension was extracted with ethyl acetate (1×200 mL, 1×100 mL). The combined organic solution was washed with brine (100 mL), dried over sodium sulfate, filtered and the filtrate concentrated under reduced pressure to give 5.12 g (100%) of 45a as an off-white solid.

Synthesis of (S)-6,7-Dimethoxy-1-(4-(trifluoromethyl) phenethyl)-1,2,3,4-tetrahydroisoquinoline (46a). This reaction also utilizes the known catalyst developed by R. Noyori, et al. (see J. Am. Chem. Soc., 1996, 118: 4916-4917). A mixture of dichloro(p-cymene)ruthenium(II) dimer (52 mg, 0.086 mmol, 0.75 mol %), 32 (68 mg, 0.17 mmol, 1.5 mol %, prepared as shown in Scheme 8) and triethylamine (0.05 mL, 0.35 mmol, 3.0 mol %) in acetonitrile (3 mL) was heated at reflux for 1 h. The mixture was cooled to rt and added to a solution of 45a (4.15 g, 11.4 mmol, 1.0 eq) in dichloromethane (30 mL) giving a yellow-brown solution. Formic acid-triethylamine, 5:2 complex, (6 mL) was added slowly via syringe. Some gas slowly evolved from the reaction mixture. The reaction mixture was stirred at rt for 2 h then quenched by the very slow addition of saturated sodium bicarbonate solution (75 mL). The mixture was transferred to a separatory funnel, diluted with dichloromethane (100 mL) and saturated sodium bicarbonate solution (50 mL) and shaken to neutralize all remaining formic acid. The organic phase was separated and the aqueous phase extracted with dichloromethane (50 mL). The combined organic solution was dried over sodium sulfate, filtered and the filtrate concentrated under reduced pressure. The residual yellow-orange viscous oil was dissolved in isopropanol (75 mL) and an approximately 5M solution of hydrogen chloride in isopropanol (6 mL) was added slowly. After several minutes, a precipitate slowly formed. The suspension was stirred at rt for 1.5 h then was filtered. The solid was washed with isopropanol (50 mL) and dried under nitrogen for 1.5 h to give 4.23 g of 46a (hydrogen chloride salt) as a tan solid. The solid was slowly dissolved in refluxing ethanol (145 mL), then the solution was allowed to cool slowly to rt and was stirred overnight. The solid was filtered, washed with a small volume of ethanol and dried under nitrogen to give a white, fluffy solid. The solid was suspended in dichloromethane (150 mL) and saturated sodium bicarbonate solution (75 mL) was added slowly with stirring. The suspension was stirred until a clear, biphasic mixture developed. The organic phase was separated, dried over sodium sulfate, filtered and the filtrate concentrated under reduced pressure. Residual dichloromethane was co-evaporated with hexanes (50 mL) to give 3.18 g (76%) of 46a as a colorless oil that slowly crystallized as a white solid. Chiral HPLC (Chiralcel OD column, isocratic elution with 90% hexanes/10% ethanol) showed 46a to be >99% ee.

Synthesis of (R)-2-((S)-6,7-Dimethoxy-1-(4-(trifluoromethyl)phenethyl) -3,4-dihydroisoquinolin-2(1H)-yl)-N-(methyl-$d_3$)-2-phenylacetamide hydrochloride (117).

DIPEA (0.55 g, 0.74 mL, 4.25 mmol, 1.25 eq) was added to a solution of 46a (1.24 g, 3.40 mmol, 1.0 eq) and 35 (1.20 g, 3.74 mmol, 1.1 eq, prepared as shown in Scheme 9) in acetonitrile (50 mL) and the mixture was heated at reflux for 20.5 h. The mixture was cooled to rt and concentrated under reduced pressure. The residual oil was dissolved in ethyl acetate (75 mL) and the solution was washed with saturated sodium bicarbonate solution (75 mL). The organic solution was dried over sodium sulfate, filtered and the filtrate concentrated under reduced pressure to give a light-brown gummy foam. The crude product was dissolved in a minimum volume of dichloromethane, adsorbed onto silica gel and dry-loaded on a column of silica gel (50 g) packed in 33% ethyl acetate/heptanes. The column was eluted with 33% ethyl acetate/heptanes (450 mL), 50% ethyl acetate/heptanes (500 mL) and 60% ethyl acetate/heptanes (1 L). Product-containing fractions were concentrated under reduced pressure to give a tan, gummy foam. The gummy foam was dissolved in tetrahydrofuran (25 mL) and an approximately 5M solution of hydrogen chloride in isopropanol (2 mL) was added. After several minutes, the mixture was concentrated under reduced pressure to give a gummy oil that was dissolved in ethyl acetate (25 mL) and re-concentrated under reduced pressure to give a tan solid. The solid was suspended in ethyl acetate (65 mL) and the mixture heated at reflux until a clear, pale-yellow solution developed (approximately 45 min). The solution was allowed to cool to rt and was stirred for 4 h. The solid was filtered and dried under nitrogen to give 0.66 g of Compound 117 as a white solid. Chiral HPLC (Chiralcel OD column, isocratic elution with 95% hexanes/5% ethanol) of the free-base of 117 showed the material to be >99% ee. $^1$H-NMR (300 MHz, CDCl$_3$): δ 1.93-2.05 (m, 1H), 2.78-2.84 (m, 2H), 3.04-3.15 (m, 2H), 3.22-3.29 (m, 1H), 3.67 (s, 3H), 3.79-3.86 (m, 2H), 3.90 (s, 3H), 3.93-3.97 (m, 1H), 4.55 (d, J=10.2, 1H), 5.74 (s, 1H), 6.69 (s, 1H), 7.10 (d, J=7.9, 2H), 7.39-7.46 (m, 5H), 7.61-7.63 (m, 2H), 9.55 (s, 1H), 12.60-12.64 (m, 1H). $^{13}$C-NMR (75 MHz, CDCl$_3$): δ 21.62, 32.14, 35.64, 43.50, 56.02, 56.09, 59.46, 71.93, 109.56, 111.61, 121.07, 121.17, 125.62, 125.66, 128.95, 129.44, 129.72, 129.83, 130.62, 143.27, 148.61, 149.74, 164.96. HPLC (method: Waters Atlantis T3 2.1×50 mm 3 μm C18-RP column—gradient method 5-95% ACN+0.1% formic acid in 14 min (1.0 mL/min) with 4 min hold at 95% ACN; Wavelength: 305 nm): retention time: 6.31 min; 99.6% purity. MS (M+H): 516.3. Elemental Analysis (C$_{29}$H$_{29}$D$_3$ClF$_3$N$_2$O$_3$): Calculated: C=63.10, H=5.84, Cl=6.42, F=10.32. Found: C=63.20, H=5.99, Cl=6.47, F=10.25.

Example 6

Synthesis of (R)-2-((S)-6,7-Di(methoxy-d$_3$)-1-(4-(trifluoromethyl)phenethyl)-3,4-dihydroisoquinolin-2(1H)-yl)-N-methyl-2-phenylacetamide hydrochloride (109). Compound 109 was prepared as generally outlined in Scheme 11 above, beginning with intermediate 46 and replacing reagent 35 with 38. Details of the synthesis are set forth below.

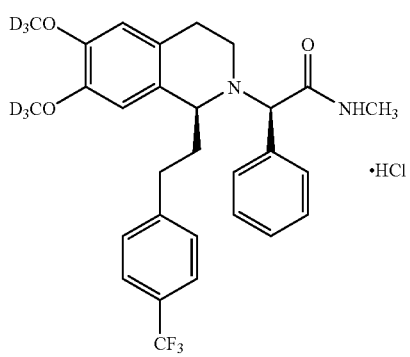

109

Synthesis of (R)-2-((S)-6,7-Di(methoxy-d$_3$)-1-(4-(trifluoromethyl)phenethyl)-3,4-dihydroisoquinolin-2(1H)-yl)-N-methyl-2-phenylacetamide hydrochloride (109). DIPEA (1.16 g, 1.6 mL, 9.0 mmol, 2.50 eq) was added to a suspension of 46 (hydrochloride salt) (1.47 g, 3.6 mmol, 1.0 eq) and 38 (1.37 g, 4.3 mmol, 1.19 eq, prepared as shown in Scheme 10) in acetonitrile (60 mL) and the mixture was heated at reflux for 19 h. The mixture was cooled to rt and concentrated under reduced pressure to yield a pale yellow-brown oil. The crude reaction product was dissolved in a minimum volume of dichloromethane, adsorbed onto silica gel and dry-loaded on a column of silica gel (65 g) packed in 33% ethyl acetate. The column was eluted with 33% ethyl acetate/heptanes (900 mL), 40% ethyl acetate/heptanes (500 mL), 50% ethyl acetate/heptanes (500 mL), and 67% ethyl acetate/heptanes (1 L). Product-containing fractions were concentrated under reduced pressure to give a foamy oil. The foamy oil was dissolved in tetrahydrofuran (30 mL) and an approximately 5M solution of hydrogen chloride in isopropanol (2 mL) was added, but no precipitate formed. After standing 5 min, the mixture was concentrated under reduced pressure to a foamy oil. The foamy oil was dissolved in ethyl acetate (30 mL) and the mixture was concentrated under reduced pressure to give a yellowish white solid. The solid was suspended in ethyl acetate (30 mL) and the mixture was heated at reflux adding ethyl acetate incrementally until a clear solution developed (a total volume of approximately 56 mL of ethyl acetate was used). The solution was allowed to cool to rt and was stirred overnight. The suspension was cooled in an ice-bath and the solid was filtered, washed with a small volume of ethyl acetate and dried under nitrogen to give 0.46 g of 109 as a white solid. Chiral HPLC (Chiralcel OD column, isocratic elution with 95% hexanes/5% ethanol) of the free-base of 109 showed the material to be >99% ee. $^1$H-NMR (300 MHz, CDCl$_3$): δ 1.91-2.04 (m, 1H), 2.72-2.84 (m, 2H), 2.89 (d, J=4.7, 3H), 3.03-3.15 (m, 2H), 3.22-3.34 (m, 1H), 3.80-3.83 (m, 2H), 3.90-4.00 (m, 1H), 4.54 (d, J=10.2, 1H), 5.74 (s, 1H), 6.68 (s, 1H), 7.10 (d, J=7.9, 2H), 7.37-7.46 (m, 5H), 7.61-7.63 (m, 2H), 9.56 (s, 1H), 12.60-12.66 (m, 1H). $^{13}$C-NMR (75 MHz, CDCl$_3$): δ 21.62, 26.79, 32.15, 35.65, 43.50, 59.46, 71.93, 109.52, 111.58, 121.04, 121.14, 125.61, 125.66, 128.95, 129.44, 129.72, 129.83, 130.62, 143.28, 148.59, 149.72, 164.92. HPLC (method: 20 mm C18-RP column—gradient method 2-95% ACN+0.1% formic acid in 3.3 min with 1.7 min hold at 95% ACN; Wavelength: 210 nm): retention time: 3.10 min; 98.3% purity. MS (M+H): 519.3. Elemental Analysis (C$_{29}$H$_{26}$D$_6$ClF$_3$N$_2$O$_3$): Calculated: C=62.76, H=5.81, Cl=6.39, N=5.05, F=10.27. Found: C=62.44, H=5.77, Cl=6.38, N=5.00, F=11.03.

Example 7

Synthesis of (R)-2-((S)-6,7-Di(methoxy-d$_3$)-1-(4-(trifluoromethyl)phenethyl)-3,4-dihydro-3,3,4,4-d$_4$-isoquinolin-2(1H)-yl)-N-(methyl-d$_3$)-2-phenylacetamide hydrochloride (105)

Compound 105 was prepared as outlined in Scheme 12 below, and as generally outlined in Scheme 11 above using appropriately deuterated reagents. All designations using the letter "b" following a compound number are in reference to the analog as found in Scheme 11. Details of the synthesis are as follows.

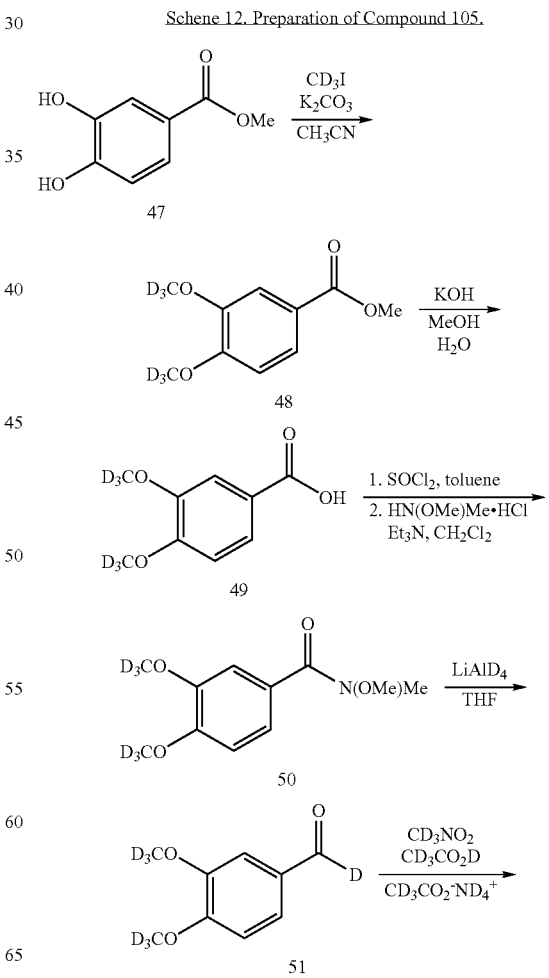

Scheme 12. Preparation of Compound 105.

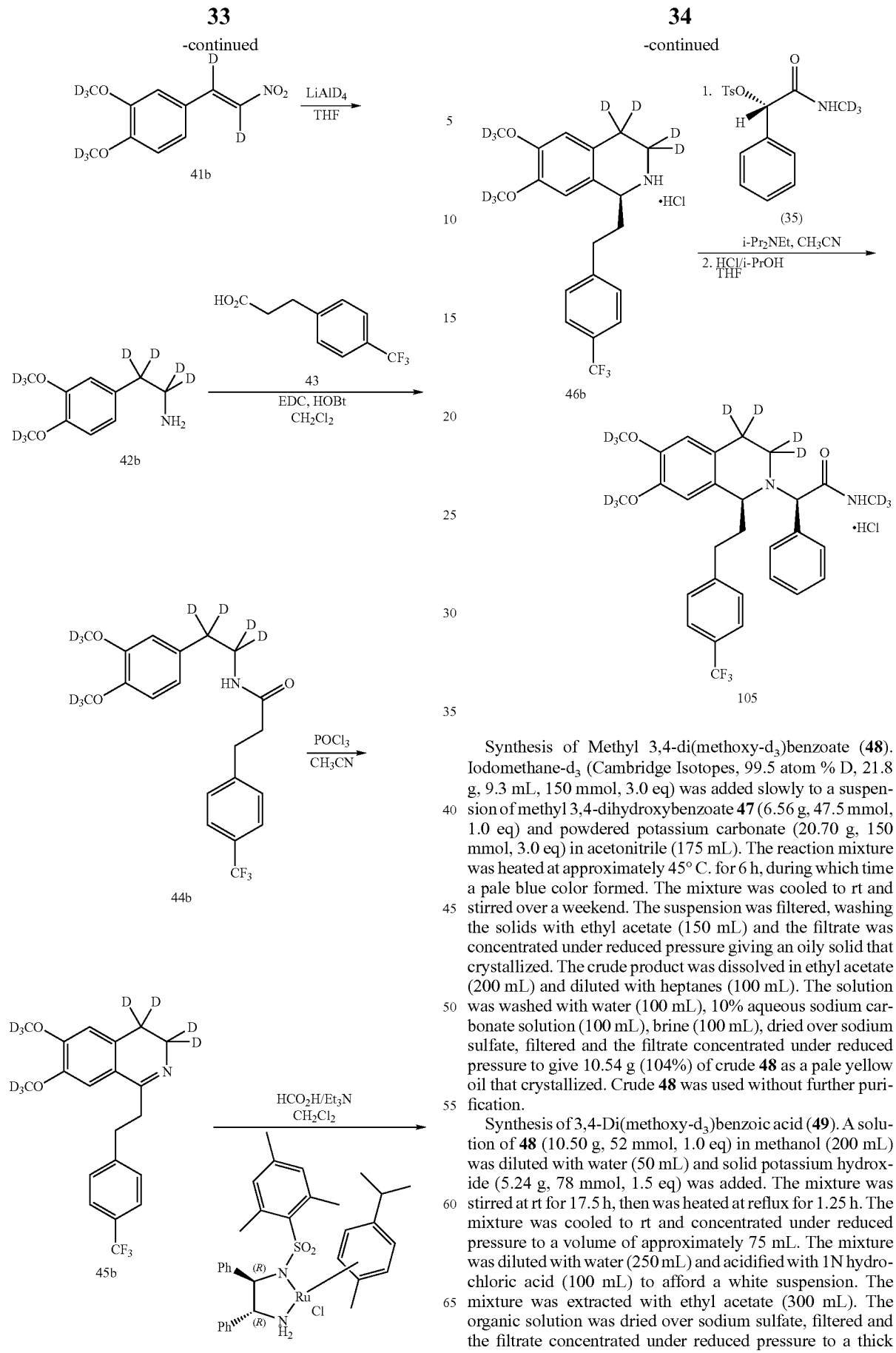

Synthesis of Methyl 3,4-di(methoxy-d₃)benzoate (48). Iodomethane-d₃ (Cambridge Isotopes, 99.5 atom % D, 21.8 g, 9.3 mL, 150 mmol, 3.0 eq) was added slowly to a suspension of methyl 3,4-dihydroxybenzoate 47 (6.56 g, 47.5 mmol, 1.0 eq) and powdered potassium carbonate (20.70 g, 150 mmol, 3.0 eq) in acetonitrile (175 mL). The reaction mixture was heated at approximately 45° C. for 6 h, during which time a pale blue color formed. The mixture was cooled to rt and stirred over a weekend. The suspension was filtered, washing the solids with ethyl acetate (150 mL) and the filtrate was concentrated under reduced pressure giving an oily solid that crystallized. The crude product was dissolved in ethyl acetate (200 mL) and diluted with heptanes (100 mL). The solution was washed with water (100 mL), 10% aqueous sodium carbonate solution (100 mL), brine (100 mL), dried over sodium sulfate, filtered and the filtrate concentrated under reduced pressure to give 10.54 g (104%) of crude 48 as a pale yellow oil that crystallized. Crude 48 was used without further purification.

Synthesis of 3,4-Di(methoxy-d₃)benzoic acid (49). A solution of 48 (10.50 g, 52 mmol, 1.0 eq) in methanol (200 mL) was diluted with water (50 mL) and solid potassium hydroxide (5.24 g, 78 mmol, 1.5 eq) was added. The mixture was stirred at rt for 17.5 h, then was heated at reflux for 1.25 h. The mixture was cooled to rt and concentrated under reduced pressure to a volume of approximately 75 mL. The mixture was diluted with water (250 mL) and acidified with 1N hydrochloric acid (100 mL) to afford a white suspension. The mixture was extracted with ethyl acetate (300 mL). The organic solution was dried over sodium sulfate, filtered and the filtrate concentrated under reduced pressure to a thick suspension. The suspension was diluted with heptanes and the solid was filtered and dried to give 8.16 g (83%) of 49 as a white solid.

Synthesis of 3,4-Di(methoxy-$d_3$)—N-methoxy-N-methyl-benzamide (50). Thionyl chloride (10.13 g, 6.2 mL, 85.1 mmol, 2.0 eq) was added to a suspension of 49 (8.00 g, 42.6 mmol, 1.0 eq) in toluene (200 mL) and the mixture was heated at reflux to provide a pale yellow solution. After 2 h at reflux the mixture was cooled to rt and stirred overnight. The mixture was concentrated under reduced pressure to give the crude acid chloride as an oil that slowly crystallized. The acid chloride was dissolved in dichloromethane (100 mL) and added over 0.25 h at 0-5° C. to a mixture of N,O-dimethyl-hydroxylamine hydrochloride (5.16 g, 53.2 mmol, 1.25 eq) and triethylamine (11.82 g, 16.3 mL, 117.0 mmol, 2.75 eq) in dichloromethane that had been pre-stirred for 0.5 h at 0-5° C. When the addition was complete the mixture was stirred for 3.5 h while warming to rt. The mixture was washed with 1N hydrochloric acid (150 mL) and saturated sodium bicarbonate solution (150 mL), then dried over sodium sulfate, filtered and the filtrate concentrated under reduced pressure to give a pale yellow oil that partially crystallized. The crude product was dissolved in a minimum volume of dichloromethane, adsorbed onto silica gel and dry-loaded on a column of silica gel (125 g) packed in 25% ethyl acetate/heptanes. The column was eluted with 25% ethyl acetate/heptanes (1 L), 40% ethyl acetate/heptanes (1 L) and 50% ethyl acetate/heptanes (2 L). Product-containing fractions were concentrated under reduced pressure to give a colorless oil that partially crystallized on standing overnight. The oily solid was triturated with hexanes (50 mL) and concentrated under reduced pressure to give 9.33 g (95%) of 50 as a white solid.

Synthesis of 3,4-Di(methoxy-$d_3$)benz(aldehyde-$d_1$) (51). A suspension of lithium aluminum deuteride (Cambridge Isotopes, 98 atom % D, 4.44 g, 105.8 mmol, 2.0 eq) in tetrahydrofuran (175 mL) was cooled in an ice-water bath. A solution of 50 (12.22 g, 52.9 mmol, 1.0 eq) in tetrahydrofuran (90 mL) was added drop-wise at 2-4° C. The suspension was stirred at 1-2° C. for 1 h, allowed to warm to rt over 0.75 h and stirred for 1.5 h. The suspension was cooled in an ice-brine bath and quenched by the very cautious addition of 2N hydrochloric acid while maintaining the internal temperature at ≦6° C. As gas evolution slowed, the mixture became very thick. Upon further addition of 2N hydrochloric acid the suspension became thinner. A total of 250 mL was used to quench the reaction. The mixture was stirred for 10 min then extracted with 2:1 ethyl acetate/heptanes (2×250 mL). The combined organic solution was washed with brine (2×100 mL), dried over sodium sulfate, filtered and the filtrate concentrated under reduced pressure to give an off-white oil. The crude product was combined with 0.29 g of crude product (from a former small-scale preparation), dissolved in a minimum volume of dichloromethane, adsorbed onto silica gel and dry-loaded on a column of silica gel (150 g) packed in heptanes. The column was eluted with heptanes (750 mL), 25% ethyl acetate/heptanes (1 L) and 30% ethyl acetate/heptanes (1.5 L). Product-containing fractions were concentrated under reduced pressure to give a pale yellow oil that slowly crystallized upon seeding. After crystallization was complete, the solid was dried under high vacuum for 1 h to give 6.10 g (67%) of 51.

Synthesis of (E)-1,2-Di(methoxy-$d_3$)-4-(2-nitro(1,2-$d_2$-vinyl))benzene (41b). A mixture of 51 (5.88 g, 34.0 mmol, 1.0 eq), nitromethane-$d_3$ (Cambridge Isotopes, 99 atom % D, 5.00 g, 4.2 mL, 78.2 mmol, 2.3 eq), ammonium acetate-$d_7$ (CDN Isotopes, 98 atom % D, 3.71 g, 44.2 mmol, 1.3 eq) and acetic acid-$d_4$ (Cambridge Isotopes, 99.5 atom % D, 36 mL) was heated at reflux for 7 h. The dark brown solution was cooled to rt and the resulting suspension was stirred overnight. The suspension was cooled in an ice-water bath and diluted with 1:1 ethanol/water (75 mL). The solid was filtered, washed with 1:1 ethanol/water (75 mL) and dried on the filter for 5 min. The solid was washed with 1:1 ethanol/heptanes (50 mL) and dried to give 4.23 g (57%) of 41b as yellow shiny crystals.

Synthesis of 2-(3,4-Di(methoxy-$d_3$)phenyl)(ethyl-$d_4$)amine (42b). A suspension of lithium aluminum deuteride (Cambridge Isotopes, 98 atom % D, 0.85 g, 20.3 mmol, 2.2 eq) in tetrahydrofuran (40 mL) was cooled in an ice-water bath. A solution of 41b (2.00 g, 9.2 mmol, 1.0 eq) in tetrahydrofuran (40 mL) was added drop-wise at ≦10° C. The mixture was allowed to warm to rt, then heated at reflux for 5 h. The light brown suspension was cooled to rt, then to approximately 10° C. The mixture was quenched at ≦10° C. by the very cautious addition of $D_2O$ (Cambridge Isotopes, 99.8 atom % D, 0.85 mL), 15% NaOD in $D_2O$ (0.85 mL, prepared from 40% NaOD in $D_2O$, Aldrich, 99 atom % D), and $D_2O$ (2.55 mL). The suspension was stirred for 1 h while warming to approximately 20° C. The suspension was filtered through a pad of Celite, washing the pad with tetrahydrofuran (100 mL). The filtrate was concentrated under reduced pressure to give 1.87 g (106%) of crude 42b as a yellow-brown oil that was used without further purification.

Synthesis of N-2-((3,4-Di(methoxy-$d_3$)phenyl)(ethyl-$d_4$)-3-(4-trifluoromethyl)phenyl)-propanamide (44b). EDC (2.06 g, 10.8 mmol, 1.2 eq) was added to a suspension of 43 (1.96 g, 9.0 mmol, 1.0 eq) and HOBt (1.00 g, 7.4 mmol, 0.82 eq) in dichloromethane (50 mL) at 0° C. The mixture was stirred at rt for 15 min to yield a clear solution. A solution of crude 42b (1.87 g, 9.0 mmol, 1.0 eq) in dichloromethane (25 mL) was added slowly. The yellow-brown solution was allowed to warm to rt and was stirred overnight. The mixture was diluted with dichloromethane (100 mL) and the solution was washed with 1N hydrochloric acid (100 mL) followed by 1N sodium hydroxide (100 mL). The organic phase was dried over sodium sulfate, filtered and the filtrate concentrated under reduced pressure to give a tan solid. The crude product was dissolved in a minimum volume of dichloromethane, adsorbed onto silica gel and dry-loaded on a column of silica gel packed in toluene. The column was eluted with toluene (300 mL), 20% ethyl acetate/toluene (500 mL), 30% ethyl acetate/toluene (500 mL), and 40% ethyl acetate/toluene (500 mL). Product-containing fractions were concentrated under reduced pressure to give an off-white solid. The solid was triturated with heptanes (75 mL), filtered and dried to give 2.11 g (60%) of 44b.

Synthesis of 6,7-Di(methoxy-$d_3$)-1-(4-(trifluoromethyl)phenethyl)-3,4-dihydro-3,3,4,4-$d_4$-isoquinoline (45b). Phosphorous oxychloride (1.73 g, 1.05 mL, 11.25 mmol, 2.2 eq) was added to a solution of 44b (2.00 g, 5.12 mmol, 1.0 eq) in acetonitrile (50 mL). The mixture was heated at reflux. After 3 h at reflux, the dark brown solution was cooled to rt and was concentrated under reduced pressure to give a dark brown oil. Methanol-d (Cambridge Isotopes, 99 atom % D, 10 mL) was added very slowly to the oil and the solution was concentrated under reduced pressure. The residual brown oil was dissolved in ethyl acetate (50 mL) and saturated sodium bicarbonate solution was added slowly with stirring until the pH of the aqueous phase remained >7. The mixture was diluted with ethyl acetate (50 mL), transferred to a separatory funnel and shaken. The organic phase was dried over sodium sulfate, filtered and the filtrate concentrated under reduced pressure to give 1.96 g of 45b as a tan solid.

Synthesis of (S)-6,7-Di(methoxy-d$_3$)-1-(4-(trifluoromethyl)phenethyl)-1,2,3,4-tetrahydro-3,3,4,4-d$_4$-isoquinoline hydrochloride (46b). A mixture of dichloro(p-cymene)-ruthenium(II) dimer (25 mg, 0.041 mmol, 0.82 mol %), 32 (32 mg, 0.082 mmol, 0.164 mol %) and triethylamine (0.02 mL, 0.27 mmol, 5.5 mol %) in acetonitrile (3 mL) was heated at reflux for 1 h. The mixture was cooled to rt and added to a solution of crude 45b (1.86 g, 5.0 mmol, 1.0 eq) in dichloromethane (50 mL) to provide a yellow-brown solution.

Formic acid-triethylamine, 5:2 complex, (2.7 mL) was added slowly via syringe. The reaction mixture was stirred at rt for 4.5 h then was quenched by the very slow addition of saturated sodium bicarbonate solution (50 mL). The mixture was transferred to a separatory funnel, diluted with dichloromethane (50 mL) and saturated sodium bicarbonate solution (25 mL) and shaken to neutralize all remaining formic acid. The organic phase was separated and the aqueous phase was extracted with dichloromethane (25 mL). The combined organic solution was dried over sodium sulfate, filtered and the filtrate concentrated under reduced pressure to give a brown oil. The oil was dissolved in ethanol (100 mL) and an approximately 5M solution of hydrogen chloride in isopropanol (2 mL) was added slowly, resulting in a thick precipitate. The suspension was heated at reflux to give a clear solution. The solution was cooled to rt and stirred overnight. The resulting suspension was cooled in an ice-bath and stirred 0.5 h. The solid was filtered, washed with cold ethanol (10 mL) and dried under nitrogen to give 1.30 g (69%) of 46b (hydrochloride salt) as a white solid. Chiral HPLC (Chiralcel OD column, isocratic elution with 90% hexanes/10% ethanol) of the free-base of 46b showed the material to be 97% of the desired enantiomer and 0.75% of the undesired enantiomer, along with 3 minor impurities. 46b (hydrochloride salt) was used without further purification.

Synthesis of (R)-2-((S)-6,7-Di(methoxy-d$_3$)-1-(4-(trifluoromethyl)phenethyl)-3,4-dihydro-(3,3,4,4-d$_4$)isoquinolin-2(1H)-yl)-N-methyl-d$_3$-2-phenylacetamide hydrochloride (105). DIPEA (0.81 g, 1.1 mL, 6.30 mmol, 2.25 eq) was added to a suspension of 46b (hydrochloride salt) (1.15 g, 2.80 mmol, 1.0 eq) and 35 (0.99 g, 3.08 mmol, 1.1 eq) in acetonitrile (50 mL) and the mixture was heated at reflux for 20.5 h. Additional DIPEA (0.18 g, 0.24 mL, 1.40 mmol, 0.5 eq) and 35 (0.45 g, 1.40 mmol, 0.5 eq) were added and the mixture was heated at reflux for an additional 4 h. The mixture was cooled to rt and concentrated under reduced pressure to a small volume. The remaining solution was partitioned between ethyl acetate (100 mL) and water (50 mL). The organic phase was washed with brine (50 mL), dried over sodium sulfate, filtered and the filtrate concentrated under reduced pressure to give an oily solid. The crude product was dissolved in a minimum volume of dichloromethane, adsorbed onto silica gel and dry-loaded on a column of silica gel (40 g) packed in 30% ethyl acetate. The column was eluted with 30% ethyl acetate/heptanes (500 mL), 40% ethyl acetate/heptanes (500 mL), 50% ethyl acetate/heptanes (500 mL), and 60% ethyl acetate/heptanes (750 mL). Product-containing fractions were concentrated under reduced pressure to give a gummy oil. The gummy oil was dissolved in ethanol (30 mL) and an approximately 5M solution of hydrogen chloride in isopropanol (2 mL) was added, but no precipitate formed. The mixture was stirred 5 min, then concentrated under reduced pressure to a volume of approximately 5 mL. The mixture was diluted with ethyl acetate (10 mL) and solids formed. The suspension was concentrated under reduced pressure to give an off-white solid. The solid was suspended in ethyl acetate (45 mL) and the mixture heated at reflux. After 0.5 h a clear solution had not developed, so more ethyl acetate (5 mL) was added and the mixture was heated a further 0.25 h to yield a clear solution. The solution was allowed to cool to rt and was stirred 1.5 h. The resulting suspension was cooled in an ice-bath and the solid was filtered, washed with a small volume of ethyl acetate and dried under nitrogen to give 0.46 g of 105 as a white solid. Chiral HPLC (Chiralcel OD column, isocratic elution with 95% hexanes/5% ethanol) of the free-base of 105 showed the material to be >99% ee. $^1$H-NMR (300 MHz, CDCl$_3$): δ 1.93-2.00 (m, 1H), 2.78-2.84 (m, 2H), 3.08-3.15 (m, 1H), 3.79-3.82 (m, 1H), 4.54 (d, J=10.5, 1H), 5.74 (s, 1H), 6.68 (s, 1H), 7.10 (d, J=7.9, 2H), 7.37-7.46 (m, 5H), 7.61-7.63 (m, 2H), 9.55 (s, 1H), 12.67 (d, J=9.1, 1H). $^{13}$C-NMR (75 MHz, CDCl$_3$): δ 32.14, 35.60, 59.45, 71.95, 109.62, 111.65, 121.04, 121.22, 125.61, 125.66, 128.96, 129.44, 129.74, 129.82, 130.60, 143.28, 148.64, 149.73, 164.96. HPLC (method: Waters Atlantis T3 2.1×50 mm 3 µm C18-RP column —gradient method 5-95% ACN+0.1% formic acid in 14 min (1.0 mL/min) with 4 min hold at 95% ACN; Wavelength: 210 nm): retention time: 6.20 min; 99.1% purity. MS (M+H): 526.2. Elemental Analysis (C$_{29}$H$_{19}$D$_{13}$ClF$_3$N$_2$O$_3$): Calculated: C=61.97, H=5.74, Cl=6.31, N=4.98, F=10.14. Found: C=62.05, H=5.75, Cl=6.43, N=4.96, F=10.28.

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay: Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich. The incubation mixtures are prepared according to Table 2:

TABLE 2

| Reaction Mixture Composition for Human Liver Microsome Study | |
|---|---|
| Liver Microsomes | 3.0 mg/mL |
| Potassium Phosphate, pH 7.4 | 100 mM |
| Magnesium Chloride | 10 mM |

Determination of Metabolic Stability: Two aliquots of this reaction mixture are used for a compound of this invention. The aliquots are incubated in a shaking water bath at 37° C. for 3 minutes. The test compound is then added into each aliquot at a final concentration of 0.5 µM. The reaction is initiated by the addition of cofactor (NADPH) into one aliquot (the other aliquot lacking NADPH serves as the negative control). Both aliquots are then incubated in a shaking water bath at 37° C. Fifty microliters (50 µL) of the incubation mixtures are withdrawn in triplicate from each aliquot at 0, 5, 10, 20, and 30 minutes and combined with 50 µL of ice-cold acetonitrile to terminate the reaction. The same procedure is followed for almorexant and the positive control, 7-ethoxycoumarin. Testing is done in triplicate.

Data analysis: The in vitro $t_{1/2}$S for test compounds are calculated from the slopes of the linear regression of % parent remaining (ln) vs incubation time relationship.

in vitro $t_{1/2}$=0.693/k k=−[slope of linear regression of % parent remaining(ln) vs incubation time]

Data analysis is performed using Microsoft Excel Software.

The metabolic stability of compounds of Formula I is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

SUPERSOMES™ Assay. Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 μM of a compound of Formula I in 100 mM potassium phosphate buffer (pH 7.4) is incubated at 37° C. in triplicate. Positive controls contain 1 μM of almorexant instead of a compound of formula I. Negative controls used Control Insect Cell Cytosol (insect cell microsomes that lacked any human metabolic enzyme) purchased from Gen-Test (Woburn, Mass., USA). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

What is claimed is:

1. A compound of the formula:

or a pharmaceutically acceptable salt thereof, wherein:
each Z is independently selected from hydrogen and deuterium;
each R is independently selected from $CD_3$, $CD_2H$, $CDH_2$, and $CH_3$; and
when each R is $CH_3$, at least one Z is deuterium.

2. The compound of claim 1, wherein $R^1$ and $R^2$ are the same.

3. The compound of claim 2, wherein each R is independently selected from $CD_3$, and $CH_3$.

4. The compound of claim 3, wherein $Z^1=Z^2$, $Z^3=Z^4$, $Z^5=Z^6$, and $Z^7=Z^8$.

5. The compound of claim 4, wherein $Z^1=Z^2=Z^3=Z^4$, and $Z^5=Z^6=Z^7=Z^8$.

6. The compound of claim 5, wherein $Z^9$ is deuterium.

7. The compound of claim 6, wherein $Z^{10}$ is deuterium.

8. The compound of claim 1, wherein the compound is selected from any one compound in the table below:

| Compound | $R^1$ | $R^2$ | $R^3$ | $Z^1$ | $Z^2$ | $Z^3$ | $Z^4$ | $Z^5$ | $Z^6$ | $Z^7$ | $Z^8$ | $Z^9$ | $Z^{10}$ |
|---|---|---|---|---|---|---|---|---|---|---|---|---|---|
| 100 | $CD_3$ | $CD_3$ | $CD_3$ | D | D | D | D | D | D | D | D | D | D |
| 101 | $CD_3$ | $CD_3$ | $CD_3$ | H | H | H | H | H | H | H | H | H | H |
| 102 | $CD_3$ | $CD_3$ | $CD_3$ | D | D | H | H | H | H | D | D | D | D |
| 103 | $CD_3$ | $CD_3$ | $CD_3$ | H | H | H | H | D | D | D | D | H | D |
| 104 | $CD_3$ | $CD_3$ | $CD_3$ | H | H | H | H | D | D | D | D | H | H |
| 105 | $CD_3$ | $CD_3$ | $CD_3$ | D | D | D | D | H | H | H | H | H | H |
| 106 | $CD_3$ | $CD_3$ | $CD_3$ | H | H | H | H | H | H | H | H | D | D |
| 107 | $CD_3$ | $CD_3$ | $CD_3$ | H | H | H | H | H | H | H | H | D | H |
| 108 | $CD_3$ | $CD_3$ | $CH_3$ | D | D | D | D | D | D | D | D | D | D |
| 109 | $CD_3$ | $CD_3$ | $CH_3$ | H | H | H | H | H | H | H | H | H | H |
| 110 | $CD_3$ | $CD_3$ | $CH_3$ | D | D | H | H | H | H | D | D | D | D |
| 111 | $CD_3$ | $CD_3$ | $CH_3$ | H | H | H | H | D | D | D | D | H | D |
| 112 | $CD_3$ | $CD_3$ | $CH_3$ | H | H | H | H | D | D | D | D | H | H |
| 113 | $CD_3$ | $CD_3$ | $CH_3$ | D | D | D | D | H | H | H | H | H | H |
| 114 | $CD_3$ | $CD_3$ | $CH_3$ | H | H | H | H | H | H | H | H | D | D |
| 115 | $CD_3$ | $CD_3$ | $CH_3$ | H | H | H | H | H | H | H | H | D | H |
| 116 | $CH_3$ | $CH_3$ | $CD_3$ | D | D | D | D | D | D | D | D | D | D |
| 117 | $CH_3$ | $CH_3$ | $CD_3$ | H | H | H | H | H | H | H | H | H | H |
| 118 | $CH_3$ | $CH_3$ | $CD_3$ | D | D | H | H | H | H | D | D | D | D |
| 119 | $CH_3$ | $CH_3$ | $CD_3$ | H | H | H | H | D | D | D | D | H | D |
| 120 | $CH_3$ | $CH_3$ | $CD_3$ | H | H | H | H | D | D | D | D | H | H |
| 121 | $CH_3$ | $CH_3$ | $CD_3$ | D | D | D | D | H | H | H | H | H | H |

-continued

| Compound | $R^1$ | $R^2$ | $R^3$ | $Z^1$ | $Z^2$ | $Z^3$ | $Z^4$ | $Z^5$ | $Z^6$ | $Z^7$ | $Z^8$ | $Z^9$ | $Z^{10}$ |
|---|---|---|---|---|---|---|---|---|---|---|---|---|---|
| 122 and | $CH_3$ | $CH_3$ | $CD_3$ | H | H | H | H | H | H | H | H | D | D |
| 123 | $CH_3$ | $CH_3$ | $CD_3$ | H | H | H | H | H | H | H | H | D | H | or a pharmaceutically acceptable salt thereof.

9. The compound of claim 1, wherein any atom not designated as deuterium is present at its natural isotopic abundance.

10. A pyrogen-free pharmaceutical composition comprising a compound of claim 1 and a pharmaceutically acceptable carrier.

11. The composition of claim 10, further comprising a second therapeutic agent useful in the treatment or prevention of a disease or a condition selected from an eating disorder, a sleep disorder and memory impairment.

12. The composition of claim 11, wherein the second therapeutic agent is useful in the treatment or prevention of a disease or a condition selected from obesity, bulimia, anorexia nervosa, insomnia, narcolepsy, sleep apnea, jetlag syndrome, and short-, middle- or long-term memory impairment.

13. A method of inhibiting the activity of OX-1 or OX-2 in a brain cell, comprising the step of contacting the cell with a compound of claim 1.

14. A method of treating a patient suffering from, or susceptible to, a disease or condition selected from an eating disorder, a sleep disorder and memory impairment comprising the step of administering to the patient in need thereof a composition of claim 10.

15. The method of claim 14, wherein the patient is suffering from, or susceptible to, a disease or condition selected from obesity, bulimia, anorexia nervosa, insomnia, narcolepsy, sleep apnea, jetlag syndrome, and short-, middle- or long-term memory impairment.

16. The method of claim 15, wherein the patient is suffering from, or susceptible to insomnia.

17. The method of claim 14, comprising the additional step of co-administering to the patient in need thereof a second therapeutic agent useful in the treatment or prevention of a disease or a condition selected from an eating disorder, a sleep disorder and memory impairment.

18. The method of claim 17, wherein the second therapeutic agent is useful in the treatment or prevention of a disease or a condition selected from obesity, bulimia, anorexia nervosa, insomnia, narcolepsy, sleep apnea, jetlag syndrome, and short-, middle- or long-term memory impairment.

19. The method of claim 18, wherein the second therapeutic agent is useful in the treatment or prevention of insomnia.

* * * * *